United States Patent
Sodeoka et al.

(10) Patent No.: US 7,351,849 B2
(45) Date of Patent: Apr. 1, 2008

(54) PROCESS FOR PRODUCING OPTICALLY ACTIVE β-AMINO ACID DERIVATIVES

(75) Inventors: Mikiko Sodeoka, Wakou (JP); Yoshitaka Hamashima, Sendai (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/567,368

(22) PCT Filed: Aug. 18, 2004

(86) PCT No.: PCT/JP2004/012156

§ 371 (c)(1),
(2), (4) Date: Apr. 11, 2006

(87) PCT Pub. No.: WO2005/016866

PCT Pub. Date: Feb. 24, 2005

(65) Prior Publication Data

US 2006/0205968 A1 Sep. 14, 2006

(30) Foreign Application Priority Data

Aug. 19, 2003 (JP) .............................. 2003-295599

(51) Int. Cl.
*C07C 205/00* (2006.01)
*C07C 229/00* (2006.01)
(52) U.S. Cl. .................... 560/20; 560/43; 560/155; 562/433; 562/533
(58) Field of Classification Search ................ 560/19, 560/20, 43, 155; 562/433, 553
See application file for complete search history.

(56) References Cited

U.S. PATENT DOCUMENTS 6,080,857 A * 6/2000 Sibi et al. ..................... 544/97

OTHER PUBLICATIONS

Li et al., Journal of organometallics 665 (2003) 250-257.*
Renzi et al., Gazzetta Chimica Italiana (1956), 86, 1332-5.*
H. Doi et al., "Chiral Ligand-Controlled Asymmetric Conjugate Addition of Lithium Amides to Enoates", Journal American Chemical Society, vol. 125, pp. 2886-2887, 2003.
W. Zhuang et al., "Catalytic enantioselective addition of aromatic amines to enones: synthesis of optically active β-amino acid derivatives", Chemical Communications, No. 12, pp. 1240-1241, 2001.
L. Fadini et al., "Ni(II) complexes containing chiral tridentate phosphines as new catalysts for the hydroamination of activated olefins", Chemical Communications, No. 1, pp. 30-31, 2003.
K. Li et al., "Air- and moisture-stable cationic (diphosphine)palladium(II) complexes as hydroamination catalysts x-ray crystal structures of two [(diphosphine)Pd(NCM3)(OH$_2$)]$^{2+}$[OTf]$_2^-$ complexes", Journal of Organometallic Chemistry, vol. 665, pp. 250-257, 2003.
K. Li et al., "Dicationic [(BINAP)Pd)(solvent)$_2$]$^{2+}$[TfO$^-$]$_2$: enantioselective hydroamination catalyst for alkenoyl-N-oxazolidinones", Chemical Communications, No. 10, pp. 1132-1133, 2003.
Y. Hamashima et al., "Amine-Salt-Controlled, Catalytic Asymmetric Conjugate Addition of Various Amines and Asymmetric Protonation", Organic Letters, vol. 6, No. 11, pp. 1861-1864, May 27, 2004.
S. Fustero et al., "New Strategy for the Stereoselective Synthesis of Fluorinated β-Amino Acids", Journal of Organic Chemistry, vol. 67, pp. 4667-4679, 2002.
M. P. Sibi et al., "Chiral Lewis Acid Catalysis in Conjugate Additions of O-Benzylhydroxylamine to Unsaturated Amides. Enantioselective Synthesis of β-Amino Acid Precursors", J. Am. Chem. Soc., vol. 120, No. 26, pp. 6615-6616, 1998.

* cited by examiner

*Primary Examiner*—Karl Puttlitz
(74) *Attorney, Agent, or Firm*—Wenderoth, Lind & Ponack, L.L.P.

(57) ABSTRACT

The present invention is to provide a method for producing the desired optically active β-amino acid derivatives of high optical purities in high yields, without requiring a step of deprotection. More particularly, the present invention relates to a method for producing an optically active β-amino acid derivative or a salt thereof represented by the formula (2):

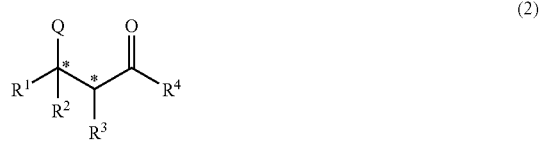

(2)

which comprises reacting an α,β-unsaturated carboxylic acid derivative or a salt thereof represented by the formula (1):

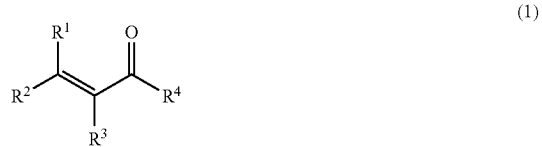

(1)

with an amines or a salt thereof in the presence of a chiral catalyst and in the presence or absence of an acid.

7 Claims, No Drawings

PROCESS FOR PRODUCING OPTICALLY ACTIVE β-AMINO ACID DERIVATIVES

This application is a U.S. national stage of International Application No. PCT/JP2004/012156 filed Aug. 18, 2004.

TECHNICAL FIELD

The present invention relates to a process for producing an optically active β-amino acid derivative useful as intermediates of medicines, agricultural chemicals, etc.

BACKGROUND ART

Previously known methods for preparing optically active β-amino acids include those in which racemates of the desired β-amino acids are first prepared and then optically resolved by using either optically active resolving agents or enzymes and those by asymmetric synthesis.

For example, non-patent reference No. 1 reports a method for producing an optically active β-amino acid derivative by reacting an aromatic secondary amine with an enone in the presence of a chiral Lewis acid.

However, such method has problems of that, for example, it requires a deprotection process to remove the alkyl group on the amino group of the obtained optically active β-amino acid derivatives, to obtain the desired product, because it makes use of secondary amines as the starting material.

Non-patent reference No. 2 reports, on the other hand, a method for the production of β-amino acids by addition of morpholine to crotonic acid esters.

However, the method also has problems of that the β-amino acids obtainable are racemates and no optically active compounds have obtained. In addition, the report says that no addition reaction product was obtainable when 3,5-bis(trifluoromethyl)aniline was made to react with cyanoolefines.

Non-patent reference No. 4 reports a method for producing β-amino acid derivatives by reacting an α,β-unsaturated carboxylic acid derivative with a primary or secondary amine in the presence of a diphosphine-palladium catalyst.

However, the non-patent reference No. 4 has neither description of trial on an asymmetric reaction nor that of optical purity of the β-amino acids obtained.

Non-patent reference No. 5 reports a method for producing β-amino acid derivatives by reacting an α,β-unsaturated carboxylic acid derivative with a primary amine in the presence of a BINAP-palladium catalyst.

However, although it has description about optical purities of the β-amino acids obtained, it has no indication of R- or S-form. Furthermore, when amines of a high nucleophilicity, for example, methoxyaniline, etc. are used, only products of low optical purities are obtained.

The non-patent reference No. 3 and patent reference No. 1 also report a method for producing β-aminoamides using a chiral Lewis acid. This method, however, is not satisfactory as an industrial production, on the one hand, because it has to be carried out practically at temperatures as low as −60° C., resulting in operational difficulty, and, on the other hand, at higher temperatures, although the yields are improved but the optical purities are thought to be lowered. Another problem in the method is that it requires more than catalytic amount, for example, more than 30 mol % of the chiral Lewis acids.

Non-patent reference No. 6 describes a method in which lithium amides are reacted with α,β-unsaturated carboxylic acid esters in the presence of chiral ligands. However, the method still has problems and is not industrially applicable one, because it requires lithiation of the amine used at very low temperature of −78° C. in order to obtain product of a high optical purity, and a chiral ligand is used in an amount of not less than one equivalent.

Non-patent reference 1: Chem. Commun., 1240 (2001).
Non-patent reference 2: Chem. Commun., 30 (2003).
Non-patent reference 3: J. American Chemical Society, 120, 6615 (1998).
Non-patent reference 4: J. Organometallic Chemistry, 665, 250 (2003).
Non-patent reference 5: Chem. Commun., 1132 (2003).
Non-patent reference 6: J. American Chemical Society, 125, 2886 (2003).
Patent reference 1: U.S. Pat. No. 6,080,857.

DISCLOSURE OF THE INVENTION

The present invention has been accomplished in consideration of the problems mentioned above, and the aim of the present invention is to provide a process for producing an optically active β-amino acid derivative, which gives the desired products of high optical purities without requiring an extra process of deprotection.

The present inventors intensively studied, in the technical field mentioned above, and found that optically active β-amino acid derivatives can be produced advantageously in view of industrial production because of high yields and optical purities of the products without requiring complex processes such as deprotection, etc., by reacting a specific α,β-unsaturated carboxylic acid derivative with an amine in the presence of a chiral catalyst (compounds of the formula (5) or (6) given below are preferable). Based on this finding, they further investigated the reaction in detail and accomplished the present invention.

Thus, the following is the description of the present invention:

1. A process for producing an optically active β-amino acid derivative of the formula (2):

wherein $R^1$ and $R^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted and a heterocyclic group which may be substituted;

$R^3$ is a hydrogen atom, an alkoxy group which may be substituted, an aryloxy group which may be substituted, an aralkyloxy group which may be substituted, a hydroxy group and a hydrocarbon group which may be substituted;

$R^4$ is an alkoxy group which may be substituted, an aryloxy group which may be substituted, an aralkyloxy group which may be substituted, a hydroxy group, —$NR^aR^b$ [wherein $R^a$ and $R^b$ are each independently a hydrogen atom, a hydrocarbon group which may be substituted and an acyl group which may be substituted, —SO$_2$A$^1$ (wherein A$^1$ is a hydrocarbon group which may be substituted or a substituted amino group), or —COOR$^c$ (R$^c$ is a hydrocarbon group which may be substituted)] or a heterocyclic group which may be substituted, and R$^1$ and R$^2$, or R$^2$ and R$^3$ each may combine to form a ring; with the proviso that when R$^1$=R$^2$, R$^3$ is then a hydrocarbon group which may be substituted;

Q stands for a group formed by removing a hydrogen atom from an amine; and

* indicates an asymmetric carbon atom;

or a salt thereof, which comprises reacting an α,β-unsaturated carboxylic acid derivative of the formula (1):

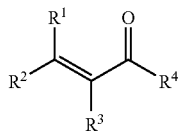

(1)

wherein R$^1$ to R$^4$ are each the same as stated above, with an amine or a salt thereof, in the presence of a chiral catalyst and in the presence or absence of an acid.

2. The process according to the above 1, wherein said amine or acid salt thereof is a compound of the formula (3):

R$^5$—NH—R$^{55}$.aX    (3)

wherein R$^5$ and R$^{55}$ are each independently a hydrogen atom, a hydrocarbon group which may be substituted, an alkoxy group which may be substituted, an aryloxy group which may be substituted or an aralkyloxy group which may be substituted; X is an acid; and a is 0 or 1.

3. The process according to the above 1, wherein said optically active β-amino acid or salt thereof is a compound of the formula (4):

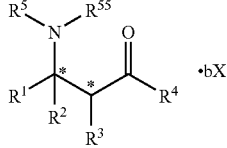

(4)

wherein R$^1$ and R$^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted or a heterocyclic group which may be substituted;

R$^3$ is a hydrogen atom, an alkoxy group which may be substituted, an aryloxy group which may be substituted, an aralkyloxy group which may be substituted, a hydroxy group or a hydrocarbon group which may be substituted;

R$^4$ is an alkoxy group which may be substituted, an aryloxy group which may be substituted, an aralkyloxy group which may be substituted, a hydroxy group, —NR$^a$R$^b$ [wherein R$^a$ and R$^b$ are each independently a hydrogen atom, a hydrocarbon group which may be substituted, an acyl group which may be substituted, —SO$_2$A$^1$ (wherein A$^1$ is a hydrocarbon group which may be substituted or a substituted amino group), or —COOR$^c$ (R$^c$ is a hydrocarbon group which may be substituted)] or a heterocyclic group which may be substituted;

R$^5$ and R$^{55}$ are each independently a hydrogen atom, a hydrocarbon group which may be substituted, an alkoxy group which may be substituted, an aryloxy group which may be substituted or an aralkyloxy group which may be substituted;

b is 0 or 1;

X is an acid;

* indicates an asymmetric carbon; or

R$^1$ and R$^2$, or R$^2$ and R$^3$ may combine to form a ring, with the proviso that when R$^1$=R$^2$, then R$^3$ is a hydrocarbon group which may be substituted.

4. The process according to the above 1, wherein the chiral catalyst is a chiral transition-metal complex of the formula (5):

[M$_2$L$_p$A$_q$]$^{y+}$(Z$^-$)$_y$    (5)

wherein L is a chiral ligand; Z$^-$ is a counter anion; A is an anionic ligand selected from the group consisting of a hydroxy group, an amide group, an alkoxy group and a halogen atom; M is a transition metal; y is 0 or 2; q is 2; p is 2 or 4, or of the formula (6):

ML$_r$B$_s$(Z$^-$)$_c$    (6)

wherein L is a chiral ligand; Z$^-$ is a counter anion; B is a water molecule or a neutral ligand; M is a transition metal; r is 1 or 2; s is 0, 1, 2, 4 or 6; c is 0, 1 or 2.

5. A process for producing an optically active β-amino acid derivative of the formula (4a):

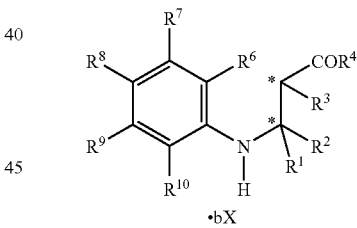

(4a)

wherein R$^1$ and R$^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted, or a heterocyclic group which may be substituted;

R$^3$ is a hydrogen atom, an alkoxy group which may be substituted, an aryloxy group which may be substituted, an aralkyloxy group which may be substituted, a hydroxy group, or a hydrocarbon group which may be substituted;

R$^4$ is an alkoxy group which may be substituted, an aryloxy group which may be substituted, an aralkyloxy group which may be substituted, a hydroxy group, —NR$^a$R$^b$ [wherein R$^a$ and R$^b$ are each independently a hydrogen atom, a hydrocarbon group which may be substituted, an acyl group which may be substituted, —SO$_2$A$^1$ (wherein A$^1$ is a hydrocarbon group which may be substituted or a substituted amino group), or —COOR$^c$ (R$^c$ is a hydrocarbon group which may be substituted)], or a heterocyclic group which may be substituted; or R$^1$ and R$^2$, or R$^2$ and R$^3$ may combine to form a ring, with the proviso that when R$^1$=R$^2$, then R$^3$ is a hydrocarbon group which may be substituted, R$^6$ to R$^{10}$ are each independently a hydrogen atom, a hydrocarbon group which may be substituted, a halogen atom, a heterocyclic group which may be substituted, an alkoxy group which may be substituted, an aralkyloxy group which may be substituted, an aryloxy group which may be substituted, an acyl group, an acyloxy group, an alkoxycarbonyl group, an aryloxycarbonyl group, an aralkyloxycarbonyl group, an alkylenedioxy group, a hydroxy group, a nitro group or an amino group which may be substituted; or R$^6$ and R$^7$, R$^7$ and R$^8$, R$^8$ and R$^9$, or R$^9$ and R$^{10}$ each may combine to form a fused ring, with the proviso that at least one of R$^6$ to R$^{10}$ is a halogenated hydrocarbon group;

X is an acid;

b is 0 or 1; and

* indicates an asymmetric carbon atom; or a salt thereof, which comprises reacting an α,β-unsaturated carboxylic acid derivative of the formula (1):

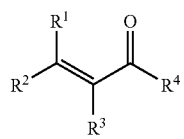

(1)

wherein R$^1$ to R$^4$ are each the same as mentioned above, with a primary amine of the formula (3b):

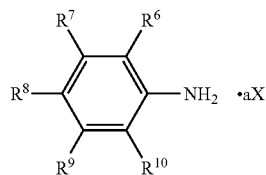

(3b)

wherein a is 0 or 1, and R$^6$ to R$^{10}$ and X are each the same as stated above, or a salt thereof in the presence or absence of an acid and in the presence of a chiral catalyst.

6. A compound of the formula (4b):

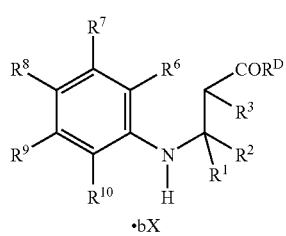

(4b)

wherein R$^1$ and R$^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted or a heterocyclic group which may be substituted;

R$^3$ is a hydrogen atom, an alkoxy group which may be substituted, an aryloxy group which may be substituted, an aralkyloxy group which may be substituted, a hydroxy group or a hydrocarbon group which may be substituted; or R$^1$ and R$^2$, or R$^2$ and R$^3$ each may combine to form a ring;

R$^6$ to R$^{10}$ are each independently a hydrogen atom, a hydrocarbon group which may be substituted, a halogen atom, a heterocyclic group which may be substituted, an alkoxy group which may be substituted, an aralkyloxy group which may be substituted, an aryloxy group which may be substituted, an acyl group which may be substituted, an acyloxy group, an alkoxycarbonyl group which may be substituted, an aryloxycarbonyl group which may be substituted, an aralkyloxycarbonyl group which may be substituted, an alkylenedioxy group, a hydroxy group, a nitro group or an amino group which may be substituted; or R$^6$ and R$^7$, R$^7$ and R$^8$, R$^8$ and R$^9$, or R$^9$ and R$^{10}$ each may combine to form a fused ring, with the proviso that at least one of R$^6$ to R$^{10}$ is a halogenated hydrocarbon group;

X is an acid;

b is 0 or 1; and

R$^D$ is a heterocyclic group which may be substituted.

Thus, since the objective compounds of the present invention are optically active β-amino acid derivatives, non-optically active β-amino acid derivatives are not the direct subject matter of the present invention.

The followings are the detailed descriptions about the individual groups in the above formulae, starting with the formula (1).

The hydrocarbon group which may be substituted and represented by R$^1$ to R$^3$ includes a hydrocarbon group and a substituted hydrocarbon group. Examples of such hydrocarbon groups include, for example, an alkyl group, an alkenyl group, an alkynyl group, an aryl group, an aralkyl group, etc.

The alkyl group may be a linear (i.e. straight), branched or cyclic alkyl group of, for example, 1 to 15, preferably 1 to 10 carbon atoms, and specific examples of such alkyl groups include methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpentyl, 3-methylpentyl, 4-methylpentyl, 2-methylpentan-3-yl, heptyl, octyl, nonyl, decyl, cyclopropyl, cyclobutyl, cyclopentyl, cyclohexyl, etc.

The alkenyl group may be a linear or branched alkenyl group of, for example, 2 to 15, preferably 2 to 10, or more preferably 2 to 6 carbon atoms, and specific examples of such alkenyl groups include ethenyl, propenyl, 1-butenyl, pentenyl, hexenyl, etc.

The alkynyl group may be a linear or branched alkynyl group of, for example, 2 to 15, preferably 2 to 10, or more preferably 2 to 6 carbon atoms, and specific examples of such alkynyl groups include ethynyl, 1-propynyl, 2-propynyl, 1-butynyl, 3-butynyl, pentynyl, hexynyl, etc.

The aryl group may be an aryl group of 6 to 14 carbon atoms, and specific examples of them include phenyl, naphthyl, anthryl, biphenyl, etc.

The aralkyl group includes those groups formed by replacing at least one hydrogen atom of the alkyl groups mentioned above with an aryl group mentioned above. Thus, for example, an aralkyl group of 7 to 12 carbon atoms is preferable. Specific examples of such aralkyl groups include benzyl, 2-phenylethyl, 1-phenylpropyl, 3-naphthylpropyl, etc.

Substituted hydrocarbon groups (hydrocarbon groups having substituent(s)) will be described hereinafter.

The alkoxycarbonyl group which may be substituted and represented by $R^1$ and $R^2$ includes an alkoxycarbonyl group and a substituted alkoxycarbonyl group.

The alkoxycarbonyl group may be a linear, branched or cyclic alkoxycarbonyl group of, for example, 2 to 19 carbon atoms, and specific examples of such alkoxycarbonyl groups include methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, etc.

The aryloxycarbonyl group which may be substituted and represented by $R^1$ and $R^2$ includes an aryloxycarbonyl group and a substituted aryloxycarbonyl group. Examples of the aryloxycarbonyl groups include, for example, those of 7 to 20 carbon atoms, and specific examples of such aryloxycarbonyl groups include phenoxycarbonyl, naphthyloxycarbonyl, etc.

The aralkyloxycarbonyl group which may be substituted and represented by $R^1$ and $R^2$ includes an aralkyloxycarbonyl group and a substituted aralkyloxycarbonyl group. The aralkyloxycarbonyl groups include those of 8 to 15 carbon atoms, and specific examples of such aralkyloxycarbonyl groups include benzyloxycarbonyl, phenylethoxycarbonyl, 9-fluorenylmethyloxycarbonyl, etc.

The acyl group which may be substituted and represented by $R^1$ and $R^2$ includes an acyl groups and a substituted acyl group. The acyl groups may be linear or branched, and include acyl groups of 1 to 18 carbon atoms derived from carboxylic acids of, for example, aliphatic carboxylic acids, aromatic carboxylic acids, etc. Specific examples of such acyl groups include formyl, acetyl, propionyl, butyryl, pivaloyl, pentanoyl, hexanoyl, lauroyl, stearoyl, benzoyl, etc.

The heterocyclic group which may be substituted and represented by $R^1$ and $R^2$ includes a heterocyclic group and a substituted heterocyclic group, and such heterocyclic groups include an aliphatic heterocyclic group and an aromatic heterocyclic group.

The aliphatic heterocyclic group includes, for example, a 5- to 8-membered, preferably 5- or 6-membered monocyclic or polycyclic or fused ring type of aliphatic heterocyclic groups containing 2 to 14 carbon atoms and at least one hetero atom, or preferably 1 to 3 hetero atoms such as, for example, nitrogen, oxygen, and/or sulfur atoms. Specific examples of such aliphatic heterocyclic groups include, for example, those groups such as 2-oxo-pyrrolidinyl, piperidino, piperazinyl, morpholino, tetrahydrofuryl, tetrahydropyranyl, etc.

The aromatic heterocyclic group includes, for example, a 5- to 8-membered, or more preferably 5- or 6-membered monocyclic or polycyclic or fused ring type of heteroaryl groups containing 2 to 15 carbon atoms and at least one hetero atom, or preferably 1 to 3 hetero atoms such as, for example, nitrogen, oxygen, and/or sulfur atoms. Specific examples of such aromatic heterocyclic groups include, for example, those groups such as furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzimidazolyl, benzoxazolyl, benzothiazolyl, etc.

The substituted heterocyclic group includes the heterocyclic groups mentioned above, at least one hydrogen atom of which is replaced by a substituent group.

The alkoxy group which may be substituted and represented by $R^1$ to $R^4$ includes an alkoxy group and a substituted alkoxy group. The alkoxy groups include a linear, branched or cyclic alkoxy group of 1 to 6 carbon atoms, and specific examples of such alkoxy groups include methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, cyclohexyloxy, etc. The substituted alkoxy group includes the above-mentioned alkoxy groups, wherein at least one hydrogen atom is replaced by a substituent group.

The aryloxy group which may be substituted and represented by $R^1$ to $R^4$ includes an aryloxy group and a substituted aryloxy group. The aryloxy group includes, for example, an aryloxy group of 6 to 14 carbon atoms, and specific examples of such aryloxy groups include phenyloxy, naphthyloxy, anthryloxy, etc. The substituted aryloxy groups include the above-mentioned aryloxy groups, wherein at least one hydrogen atom is replaced by a substituent group.

The aralkyloxy group which may be substituted and represented by $R^1$ to $R^4$ includes an aralkyloxy group and a substituted aralkyloxy group, and the aralkyloxy groups include, for example, those of 7 to 12 carbon atoms. Specific examples of such aralkyloxy groups include benzyloxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy, etc. The substituted aralkyloxy groups include the above-mentioned aralkyloxy groups, wherein at least one hydrogen atom is replaced by a substituent group.

In —$NR^aR^b$ as $R^4$, the "hydrocarbon group which may be substituted" and "acyl group which may be substituted" represented by $R^a$ and $R^b$ are the same as the "hydrocarbon group which may be substituted" described above for $R^1$ to $R^3$ and the "acyl group which may be substituted" described above for $R^1$ to $R^2$, respectively. Specific examples of —$NR^aR^b$ include amino, methylamino, dimethylamino, diethylamino, dipropylamino, diisopropylamino, N-acetylamino, N-benzoylamino, etc.

In —$SO_2A^1$ as $R^a$ and $R^b$, the "hydrocarbon group which may be substituted" represented by $A^1$ is also the same as the "hydrocarbon group which may be substituted" described above for $R^1$ to $R^3$. The substituted amino groups will be described hereinafter and are preferably those wherein two hydrogen atoms of the amino group are substituted with a substituent group such as a protective group. Specific examples of —$SO_2A^1$ include —$SO_2CH_3$, —$SO_2C_6H_5$, —$SO_2C_6H_4CH_3$, —$SO_2CF_3$, and —$SO_2N(CH_3)_2$, etc.

In —$COOR^c$ as $R^a$ and $R^b$, the "hydrocarbon group which may be substituted" represented by $R^c$ is also the same as the "hydrocarbon group which may be substituted" described above for $R^1$ to $R^3$. Specific examples of —$COOR^c$ include methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, phenoxycarbonyl, naphthyloxycarbonyl, benzyloxycarbonyl, phenylethoxycarbonyl, 9-fluorenylmethyloxycarbonyl, etc.

$R^4$ is preferably —$NR^aR^b$, wherein $R^a$ is —$COOR^c$ (wherein $R^c$ is the same as mentioned above) and $R^b$ is a hydrogen atom, namely —$NHCOOR^c$ (wherein $R^c$ is the same as mentioned above), and specific examples of them include methyl carbamate, ethyl carbamate, etc.

The substituted hydrocarbon group includes the above-mentioned hydrocarbon groups, wherein at least one hydrogen atom of the above-mentioned hydrocarbon groups is replaced by a substituent group. The term "substituent group" has the same meaning to the groups other than the hydrocarbon groups as to the hydrocarbon groups.

Furthermore, in the present invention, examples of the substituent groups in various substituted groups such as substituted heterocyclic groups, substituted hydrocarbon groups and substituted acyl groups include hydrocarbon groups, substituted hydrocarbon groups, aliphatic heterocyclic groups, substituted aliphatic heterocyclic groups, aromatic heterocyclic groups, substituted aromatic heterocyclic groups, alkoxy groups, substituted alkoxy groups, aryloxy groups, substituted aryloxy groups, aralkyloxy groups, substituted aralkyloxy groups, alkoxycarbonyl groups, aryloxycarbonyl groups, aralkyloxycarbonyl groups, acyl groups, acyloxy groups, alkylthio groups, aralkylthio groups, arylthio groups, halogen atoms, halogenated hydrocarbon groups, alkylenedioxy groups, amino groups, substituted amino groups, a cyano group, a nitro group, a hydroxy group, a carboxyl group, a sulfo group and substituted silyl groups.

The hydrocarbon groups as the substituent groups mentioned above are the same as the hydrocarbon groups described above for $R^1$ to $R^3$. The aliphatic heterocyclic groups, aromatic heterocyclic groups, alkoxycarbonyl groups, aryloxycarbonyl groups, aralkyloxycarbonyl groups and acyl groups are each the same as those groups described above for $R^1$ and $R^2$. The alkoxy groups, aryloxy groups and aralkyloxy groups are the same as those described above for $R^1$ to $R^4$.

The acyloxy group as the substituent group mentioned above includes an acyloxy group of, for example, 2 to 18 carbon atoms derived from carboxylic acids such as aliphatic carboxylic acids, aromatic carboxylic acids, etc., and specific examples of such acyloxy groups include acetoxy, propionyloxy, butyryloxy, pivaloyloxy, pentanoyloxy, hexanoyloxy, lauroyloxy, stearoyloxy, benzoyloxy, etc.

The term "alkyl", "aralkyl" and "aryl" in the alkylthio, aralkylthio and arylthio groups as the substituent groups mentioned above are respectively the same as the "alkyl groups", "aralkyl groups" and "aryl groups" described above for $R^1$ to $R^3$.

The halogen atom as the substituent group mentioned above includes fluorine, chlorine, bromine, and iodine atoms.

The halogenated hydrocarbon group as the substituent group mentioned above includes those hydrocarbon groups mentioned above, wherein at least one hydrogen atom of the hydrocarbon groups is halogenated (e.g., fluorinated, chlorinated, brominated or iodinated, and so on). Examples of the halogenated hydrocarbons include, for example, halogenated alkyl groups, and examples of the halogenated alkyl groups include those of 1 to 10 carbon atoms. Specific examples of them include chloromethyl, bromomethyl, 2-chloroethyl, 3-bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoropentyl, perfluoroisopentyl, perfluoro-tert-pentyl, perfluoro-n-hexyl, perfluoroisohexyl, perfluoroheptyl, perfluorooctyl, perfluorononyl, perfluorodecyl, 2-perfluorooctylethyl, perfluorocyclopropyl, perfluorocyclopentyl, perfluorocyclohexyl, etc.

In cases where the substituent group is an alkylenedioxy group, two adjacent hydrogen atoms on the above-mentioned, for example, aromatic ring of the aryl or aralkyl group are replaced by an alkylenedioxy group. Examples of the alkylenedioxy groups include alkylenedioxy groups of 1 to 3 carbon atoms, specific examples of them being methylenedioxy, ethylenedioxy, trimethylenedioxy, propylenedioxy, etc.

The substituted amino group as the substituent group mentioned above includes an amino groups, one or two hydrogen atoms of which are replaced with a substituent group such as protecting groups, etc. Any protecting groups can be employed if they can be used as an amino-protecting group, for example, those described as the amino-protecting groups in "PROTECTIVE GROUPS IN ORGANIC SYNTHESIS THIRD EDITION (JOHN WILEY & SONS, INC.)". Specific examples of such amino-protecting groups include alkyl groups, aryl groups, aralkyl groups, acyl groups, alkoxycarbonyl groups, aryloxycarbonyl groups, aralkyloxycarbonyl groups, etc.

The alkyl, aryl and aralkyl groups of the amino-protecting groups mentioned above are the same as those described above for the $R^1$ to $R^3$, respectively, and the acyl, alkoxycarbonyl, aryloxycarbonyl and aralkyloxycarbonyl groups are the same as those described above for the $R^1$ and $R^2$, respectively. Specific examples of the amino groups substituted by alkyl group(s), namely, the alkyl-substituted amino groups include mono or dialkylamino groups such as N-methylamino, N,N-dimethylamino, N,N-diethylamino, N,N-diisopropylamino, N-cyclohexylamino, etc. Specific examples of the amino groups substituted by aryl group(s), namely, the aryl-substituted amino groups include mono or diarylamino groups such as N-phenylamino, N,N-diphenylamino, N-naphthylamino, N-naphthyl-N-phenylamino, etc. Specific examples of the amino groups substituted by aralkyl group(s), namely, the aralkyl-substituted amino groups include mono or diaralkylamino groups such as N-benzylamino, N,N-dibenzylamino, etc. Specific examples of the amino groups substituted by acyl group(s), namely, the acylamino groups include groups such as formylamino, acetylamino, propionylamino, pivaloylamino, pentanoylamino, hexanoylamino, benzoylamino, etc. Specific examples of the amino groups substituted by alkoxycarbonyl group(s), namely, the alkoxycarbonylamino groups include methoxycarbonylamino, ethoxycarbonylamino, n-propoxycarbonylamino, n-butoxycarbonylamino, tert-butoxycarbonylamino, pentyloxycarbonylamino, hexyloxycarbonylamino, etc. Specific examples of the amino groups substituted by aryloxycarbonyl group(s), namely, the aryloxycarbonylamino groups include amino groups wherein one hydrogen atom of the amino group is replaced by an aryloxycarbonyl group. Specific examples of them include phenoxycarbonylamino, naphthyloxycarbonylamino, etc. Specific examples of the amino groups substituted by aralkyloxycarbonyl group, namely, the aralkyloxycarbonylamino groups include benzyloxycarbonylamino group, etc.

Examples of the substituted silyl groups include tri-substituted silyl groups, in which the three hydrogen atoms on the silyl group are substituted by the substituent groups of alkyl groups, aryl groups and aralkyl groups for $R^1$ to $R^3$ as mentioned above. Specific examples of such substituted silyl groups include trimethylsilyl, tert-butyldimethylsilyl, tert-butyldiphenylsilyl, triphenylsilyl, etc.

The substituted alkoxy group represented by $R^1$ to $R^4$ includes the alkoxy groups mentioned above, wherein at least one hydrogen atom of the alkoxy group is replaced by a substituent group mentioned above, namely, such as an alkyl group, a halogenated hydrocarbon group, an alkoxy group, a halogen atom, an amino group or a substituted amino group. These substituent groups are the same as those described above.

The substituted aryloxy group represented by $R^1$ to $R^4$ includes the aryloxy groups mentioned above, wherein at least one hydrogen atom of the aryloxy group is replaced by a substituent group mentioned above, namely, such as an alkyl group, a halogenated hydrocarbon group, an alkoxy group, a halogen atom, an amino group or a substituted amino group, or wherein two adjacent hydrogen atoms of the aryloxy group are replaced by an alkylenedioxy group, etc. These substituent groups are the same as those described above.

The substituted aralkyloxy group represented by $R^1$ to $R^4$ includes the aralkyloxy group mentioned above, wherein at least one hydrogen atoms of the aralkyloxy group is replaced by the substituent group mentioned above, namely, such as an alkyl group, a halogenated hydrocarbon group, an alkoxy group, a halogen atom, an amino group or a substituted amino group, or wherein two adjacent hydrogen atoms of the aralkyloxy group are replaced by an alkylenedioxy group, etc. These substituent groups are the same as those described above.

The substituted acyl group represented by $R^1$ to $R^2$ includes the acyl groups mentioned above, wherein at least one hydrogen atom of the acyl group is replaced by a substituent group mentioned above.

The substituted hydrocarbon group as a substituent group and as the substituted hydrocarbon groups in $R^1$ to $R^3$, $R^a$ to $R^c$ and $A^1$ includes the hydrocarbon groups derived from the hydrocarbon groups described for $R^1$ to $R^3$ above by replacing at least one hydrogen atom on them is replaced by a substituent group mentioned above.

The substituted hydrocarbon group represented by $R^1$ to $R^3$, $R^a$ to $R^c$, $A^1$ and the "substituent groups" include substituted alkyl groups, substituted alkenyl groups, substituted alkynyl groups, substituted aryl groups and substituted aralkyl groups.

The substituted alkyl group includes the alkyl groups described above for $R^1$ to $R^3$, wherein at least one hydrogen atom of the alkyl group is replaced by a substituent group mentioned above.

The hydrocarbon groups substituted by a halogen atom, namely, the halogenated hydrocarbon groups are the same as the "halogenated hydrocarbon groups" described above for the substituent groups.

The substituted aryl groups includes the aryl groups mentioned above, wherein at least one hydrogen atom of the aryl group is replaced by a substituent group mentioned above, or two adjacent hydrogen atoms on the aryl group are replaced by an alkylenedioxy group. The alkylenedioxy groups are the same as the "alkylenedioxy groups" described above for the substituent groups. Specific examples of the aryl groups substituted with alkyl group(s) include a tolyl group, a xylyl group, a mesityl group, etc.

The substituted aralkyl group includes the aralkyl groups mentioned above, wherein at least one hydrogen atom of the aralkyl group is replaced by a substituent group mentioned above, or two adjacent hydrogen atoms on the aryl group are replaced by an alkylenedioxy group. The alkylenedioxy groups are the same as, the "alkylenedioxy groups" described above for the substituent groups.

The heterocyclic group which may have substituent groups and designated by $R^4$ includes a cyclic group which contains at least one heteroatom such as nitrogen, oxygen and/or sulfur atoms, etc. as the ring-constituting atom. The ring may be either a monocyclic, polycyclic or fused one, and may have substituent(s) mentioned above. Preferable examples of the heterocyclic groups include those shown by the formulae below:

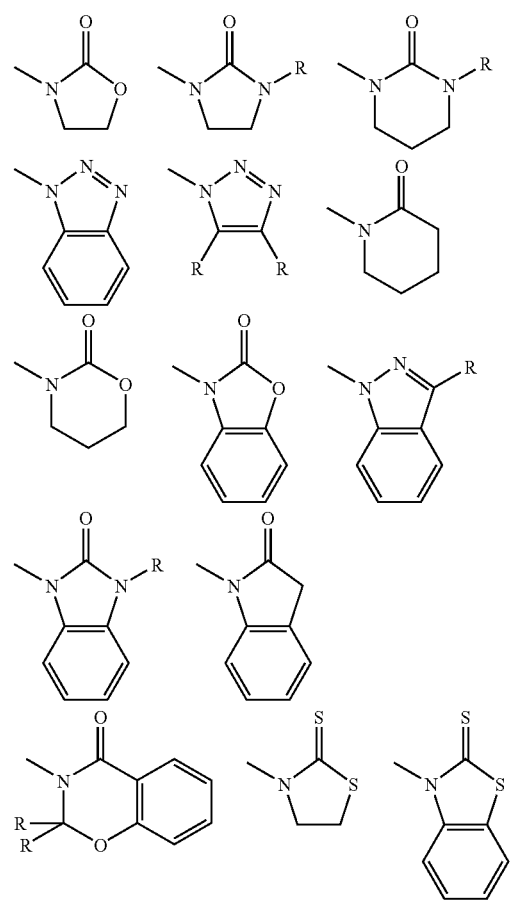

In the formula above, R is, the same or different, a hydrogen atom or a hydrocarbon group. The hydrocarbon group is the same as the "hydrocarbon group" described above for $R^1$ to $R^3$. The heterocyclic groups shown above may have substituent groups in addition to R indicated above.

$R^3$ is preferably a hydrogen atom, an alkoxy group which may be substituted, an aryloxy group which may be substituted, an aralkyloxy group which may be substituted and a hydrocarbon group which may be substituted.

Examples of the rings which may be formed from $R^1$ and $R^2$ or $R^2$ and $R^3$ combined together with the carbon atom to which they bind include, when $R^1$ and $R^2$ taken together to form a ring, a cyclobutane ring, a cyclopentane ring, a cyclohexane ring and a cycloheptane ring, and when $R^2$ and $R^3$ combine to form a ring, a cyclobutene ring, a cyclopentene ring, a cyclohexene ring and a cycloheptene ring.

Specific examples of α,β-unsaturated carboxylic acid derivatives represented by the formula (1) include α,β-unsaturated carboxylic acid esters such as methyl methacrylate, ethyl methacrylate, isopropyl methacrylate, benzyl methacrylate, methyl crotonate, ethyl crotonate, dimethyl maleate, diethyl maleate, dimethyl fumarate, diethyl fumarate, methyl 2-pentenoate, ethyl 2-pentenoate, butyl 2-pentenoate, etc.; N-acyl-α,β-unsaturated carboxylic acid amides such as N-acetylmethacrylamide, etc.; α,β-unsaturated carboxylic acid amides such as N,N-dimethylmethacrylamide, 2-pentenamide, N,N-dimethylpentenamide, etc.; α,β-unsaturated acyl carbamates such as N-methoxycarbonylmethacrylamide, N-ethoxycarbonylmethacrylamide, N-benzyloxycarbonylmethacrylamide, methyl 2-pentenoylcarbamate, etc.; α,β-unsaturated carboxylic acids such as methacrylic acid, crotonic acid, 2-pentenoic acid, 2-hexenoic acid, etc., (these acids may be in the form of salt, including alkali metal salt such as a sodium salt, a potassium salt, etc., and an ammonium salt.).

Furthermore, specific examples of the α,β-unsaturated carboxylic acid derivatives represented by the formula (1) include, for example, 3-(2-pentenoyl)-1,3-oxazolidin-2-one and one of the compounds shown below.

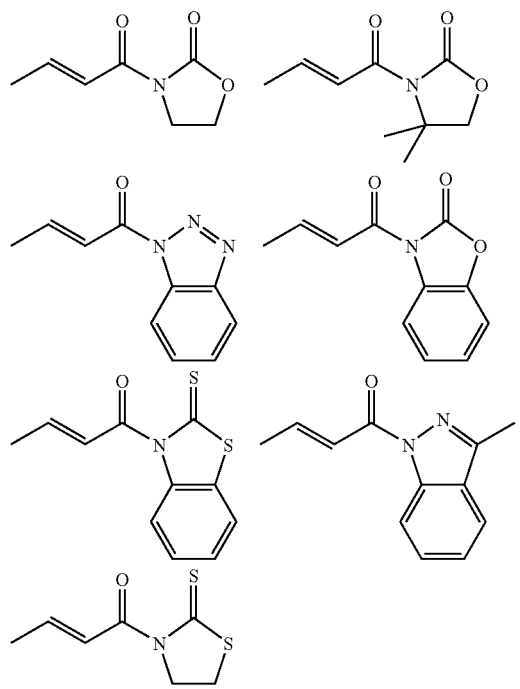

Among them, methyl 2-pentenoylcarbamate, 3-crotonoyl-1,3-oxazolidin-2-one, 3-(2-pentenoyl)-1,3-oxazolidin-2-one, etc. are especially preferable.

In the formula (2), Q is a monovalent group formed by removing one hydrogen atom from amines, and the amines which can act as Q are ammonia and the compounds represented by Formula (3). The compounds represented by the formula (3) may be both primary and secondary amines. The primary amines are, preferably, those compounds represented by the formula (3a),

wherein $R^5$ is a hydrocarbon group which may be substituted, an alkoxy group which may be substituted, an aryloxy group which may be substituted or an aralkyloxy group which may be substituted; X is an acid; and a is 0 or 1.

The secondary amines are compounds represented by Formula (3), wherein both $R^5$ and $R^{55}$ are the same or different groups other than a hydrogen atom.

"Hydrocarbon groups which may be substituted" represented by $R^5$ and $R^{55}$ in the formulae (3) and (3a), are the same as the "hydrocarbon groups" and "substituted hydrocarbon groups" described above for $R^1$ to $R^3$. "Alkoxy groups which may be substituted", "aryloxy groups which may be substituted" and "aralkyl groups which may be substituted" are also the same as the "alkoxy groups", "substituted alkoxy groups", "aryloxy groups", "substituted aryloxy groups", "aralkyloxy groups" and "substituted aralkyloxy groups" described above for $R^1$ to $R^4$.

Here, $R^5$ and/or $R^{55}$ are preferably substituted hydrocarbon groups, or especially preferably halogenated hydrocarbon-substituted hydrocarbon groups, when the production method of the present invention is carried out using amines of the formula (3) wherein a=0 and in the absence of acid.

The halogenated hydrocarbon-substituted hydrocarbon groups mean hydrocarbon groups substituted with halogenated hydrocarbon groups. However, they may have additional substituents including halogenated hydrocarbon-substituted hydrocarbon groups and substituted halogenated hydrocarbon-substituted hydrocarbon groups. The hydrocarbon groups in the halogenated hydrocarbon-substituted hydrocarbon groups, and the halogen atoms and hydrocarbon groups in the halogenated hydrocarbon groups are the same as those mentioned above.

The halogenated hydrocarbon-substituted hydrocarbon groups include hydrocarbon groups, wherein at least one hydrogen atom of the above hydrocarbon group is replaced with a halogenated hydrocarbon group. Specific examples of the halogenated hydrocarbon-substituted aliphatic hydrocarbon groups include halogenated hydrocarbon-substituted aliphatic hydrocarbon groups such as 2,2,2-trifluoroethyl, 3,3,3-trifluoropropyl, 2-perfluorooctylethyl, etc., and halogenated hydrocarbon-substituted aromatic hydrocarbon groups such as 2-trifluoromethylphenyl, 3-trifluoromethylphenyl, 4-trifluoromethylphenyl, 2-pentafluoroethylphenyl, 3-pentafluoroethylphenyl, 4-pentafluoroethylphenyl, perfluoro-n-propylphenyl, perfluoroisopropylphenyl, perflurobutylphenyl, perfluoropentylphenyl, perfluorohexylphenyl, perfluoroheptylphenyl, perfluorooctylphenyl, perfluorononylphenyl, perfluorodecylphenyl, 2-perfluorooctylethylphenyl, perfluorocyclohexylphenyl, etc.

The substituted halogenated hydrocarbon-substituted hydrocarbon group includes a halogenated hydrocarbon-substituted hydrocarbon group, wherein at least one hydrogen atom or halogen atom of the hydrocarbon group in the above-mentioned substituted halogenated hydrocarbon-substituted hydrocarbon group is replaced by a substituent group other than the halogenated hydrocarbon group. The substituent groups are the same as those described above for each group in the formula (1).

The alkoxy group which may be substituted and represented by $R^5$ and $R^{55}$ includes an alkoxy group and a substituted alkoxy group. The aryloxy group which may be substituted includes an aryloxy group and a substituted aryloxy group. The aralkyloxy group which may be substituted includes an aralkyloxy group and a substituted aralkyloxy group. These alkoxy groups, substituted alkoxy groups, aryloxy groups, substituted aryloxy groups, aralkyloxy groups and substituted aralkyloxy groups are the same as those described above for each group in the formula (1).

The amines mentioned above include primary and secondary amines represented by the above formula (3). The primary amines include amines represented by the above formula (3a), namely the formula (3) wherein $R^{55}$ is a hydrogen atom. Specific and preferable examples of such primary amines include alkylamines such as methylamine, ethylamine, propylamine, cyclohexylamine, etc.; hydroxylamines such as O-benzyl-hydroxylamine, O-methylhydroxylamine, etc.; halogenated alkyl-substituted amines such as 1H,1H-heptafluorobutylamine, 1H,1H-tridecafluoroheptylamine, 1H,1H-pentadecafluorooctylamine, 1H,1H-heptadecafluorononylamine, etc.; anilines such as aniline, 3,4-difluoroaniline, 3,5-dichloroaniline, 2,3,4-trichloroaniline, 2,4,5-trichloroaniline, 3,4,5-trichloroaniline, 2,4-dibromoaniline, 2,5-dibromoaniline, 3,4,5-tribromoaniline, 4-iodoaniline, 3-iodoaniline, 2-iodoaniline, 2-methoxyaniline, 3-methoxyaniline, 4-methoxyaniline (also called anisidine), etc., and the compounds represented by the formula (3b):

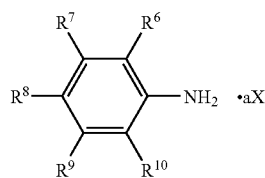

wherein $R^6$ to $R^{10}$ are each independently a hydrogen atom, a hydrocarbon group which may be substituted, a halogen atom, a heterocyclic group which may be substituted, an alkoxy group which may be substituted, an aralkyloxy group which may be substituted, an aryloxy group which may be substituted, an acyl group which may be substituted, an acyloxy group, an alkoxycarbonyl group which may be substituted, an aryloxycarbonyl group which may be substituted, an aralkyloxycarbonyl group which may be substituted, an alkylenedioxy group, a hydroxy group, a nitro group and an amino group which may be substituted; X is an acid; a is 0 or 1. $R^6$ and $R^7$, $R^7$ and $R^8$, $R^8$ and $R^9$, or $R^9$ and $R^{10}$ may also combine to form a fused ring, with the proviso that at least one of $R^6$ to $R^{10}$ is a halogenated hydrocarbon group.

Therefore, the hydrocarbon groups which may have substituents represented by $R^6$ to $R^{10}$, halogen atoms, heterocyclic groups which may be substituted, alkoxy groups which may be substituted, aralkyloxy groups which may be substituted, aryloxy groups which may be substituted, acyl groups which may be substituted, acyloxy groups, alkoxycarbonyl groups which may be substituted, aryloxycarbonyl groups which may be substituted, aralkyloxycarbonyl groups which may be substituted, alkylenedioxy groups and amino groups which may be substituted are each the same as the corresponding groups described above for $R^1$ and $R^2$ of the formula (1), respectively.

Examples of the fused rings which may be formed by the combination of each of $R^6$ and $R^7$, $R^7$ and $R^8$, $R^8$ and $R^9$, or $R^9$ and $R^{10}$ include indene, naphthalene, benzofuran, indazole, quinoline, isoquinoline, etc.

Examples of the compounds represented by the formula (3b) include 4-trifluoromethylaniline, 3-trifluoromethylaniline, 2-trifluoromethylaniline, 3,5-bis(trifluoromethyl)aniline, 2,5-bis(trifluoromethyl)aniline, 3,4,5-tris(trifluoromethyl)aniline, 4-pentafluroethylaniline, 3-pentafluoroethylaniline, 2-pentafluoroethylaniline, 2,4-diperfluoropropylaniline, 2,3-diperfluoropropylaniline, 3,5-diperfluoropropylaniline, 2,3,4-triperfluorobutylaniline, 2,4,5-triperfluoropentylaniline, 4-perfluorohexylaniline, 4-trichloromethylaniline, 3-trichloromethylaniline, 2-trichloromethylaniline, 3,4-dipentachloroethylaniline, 4-tribromomethylaniline, 3-tribromomethylaniline, 2-tribromomethylaniline, etc. Among the appropriate primary amines, aniline, anisidine and 4-trifluoromethylaniline, etc. are especially preferable.

Specific examples of the secondary amines include dimethylamine, diethylamine, dipropylamine, diisopropylamine, dicyclohexylamine, dibenzylamine, N-methylaniline, etc.

The primary and secondary amines mentioned above may be in the form of acid salts, and the acids in these acid salts may be those described below.

In the formulae (2), (4), (4a) and (4b), when $R^1=R^2$, then the carbon atom to which both $R^1$ and $R^2$ are attached cannot be an asymmetric carbon, and when $R^3$ is a hydrogen atom, the carbon atom to which $R^3$ binds cannot be an asymmetric carbon.

The optically active β-amino acid derivatives of the formula (2) above, which can be obtained by the production method of the present invention, are the optically active β-amino acid derivatives of the formula (4), when the compounds of the above formula (3) are used as the amine. When the compounds of the formula (3a) are used as the amine, there are obtained the optically active β-amino acid derivatives of the formula (4-1) below:

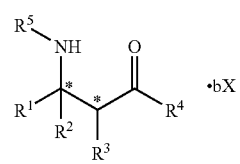

wherein $R^1$, $R^2$, $R^3$, $R^4$, $R^5$, X, b and * have the same meanings as those mentioned above.

Specific examples of the optically active β-amino acid derivatives of the formula (2), which can be obtained by the production method of the present invention, include 3-(4-trifluoromethylanilino)butyryl-1,3-oxazolidin-2-one, 3-(2-trifluoromethylanilino)butyryl-1,3-oxazolidin-2-one, 3-(4-trifluoromethylanilino)butyryl-1,3-oxazolidin-2-one, 3-[3-(4-trifluoromethyl-2-methoxyphenylamino)butyryl]oxazolidinone, methyl [3-(4-trifluoromethylphenylamino)pentanoyl]carbamate, 3-(4-trifluoromethylanilino)pentenoyl-1,3-oxazolidin-2-one, 3-(3-phenylaminobutyryl)oxazolidin-2-one, etc.

Among the optically active β-amino acid derivatives of the above formula (4a) obtainable by the production method of the present invention, those in which $R^4$ in the above formula (4a) is an alkoxy group which may be substituted, an aryloxy group which may be substituted, an aralkyloxy group which may be substituted, a heterocyclic group which may be substituted, a group represented by —$NR^aR^b$ in which $R^a$ is —$COOR^c$ (wherein $R^c$ is the same group as described for $R^4$ above) and $R^b$ is a hydrogen atom, namely a —$COOR^c$ (wherein $R^c$ is the same group as described above for $R^4$) are more preferable.

Among the compounds of the present invention represented by the above formula (4b), the optically active compounds of the formula (4c):

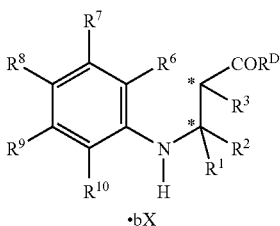

(4c)

wherein $R^1$ to $R^3$, $R^6$ to $R^{10}$, $R^D$, X, b and * have the same meanings as described above, are more preferable.

In the formulae (4b) and (4c), "heterocyclic groups which may be substituted" represented by $R^D$ are the same as the "heterocyclic groups and substituted heterocyclic groups" described above for $R^1$, $R^2$ and $R^4$.

At least one of $R^6$ to $R^{10}$ in each of the above formulae (3b) and (4a), and the above formulae (4b) and (4c) of the present invention is a halogenated hydrocarbon group. The halogenated hydrocarbon groups are the same as those described above as substituents for $R^6$ to $R^{10}$. The preferable halogenated hydrocarbon group is a halogenated alkyl group.

Chiral catalysts which may be preferably used in the present invention include, for example, either chiral transition metal complexes of the formula (5) below:

$$[M_2L_pA_q]^{y+}(Z^-)_y \quad (5)$$

wherein L is a chiral ligand; $Z^-$ is a counter anion; A is preferably a monovalent anionic ligand selected from the group consisting of a hydroxy group, an amide group, an alkoxy group and a halogen atom; M is a transition metal; y is 0 or 2; q is 2; p is 2 or 4, or chiral transition metal complexes of the formula (6):

$$ML_rB_s(Z^-)_c \quad (6)$$

wherein L is a chiral ligand; $Z^-$ is preferably a counter anion; B is water or a neutral ligand; M is a transition metal; r is 1 or 2; s is 0, 1, 2, 4 or 6; c is 0, 1 or 2.

The following is the description for each group in the formulae (5) and (6): examples of the anionic ligands represented by A include, including the preferable examples described above, for example, $H^-$, $OH^-$, $[OR']^-$, $[R'HN]^-$, $[R'_2N]^-$, $H_2N^-$, $[R'_3SiO]^-$, $F^-$, $Br^-$, $Cl^-$, $I^-$, $I_3^-$, $NH_2CO^-$, $CO^-$, $CH_3COO^-$, $CF_3COO$—, $CF_3CF_2COO^-$, $CF_3CF_2CF_2COO^-$, $CF_3SO_3-$, $p\text{-}CH_3C_6H_4SO_3^-$, $ClO_4^-$, $NO_3^-$, $SO_4^{2-}$, $CO_3^{2-}$, $PO_4^{3-}$, $BF_4^-$, $B(C_6H_5)_4^-$, $B[3,5\text{-}(CF_3)_2C_6H_3]_3^-$, $PF_6^-$, $SbF_6^-$, $AsF_6^-$, $(CH_3COCHCOCH_3)^-$, etc. In the anionic ligands, monovalent anionic ligands are preferable. R' will be described below.

Examples of the transition metals represented by M include, for example, elements of Families 8 to 11 of the periodic table, or more specifically, transition metals such as gold (Au), silver (Ag), copper (Cu), cobalt (Co), iridium (Ir), nickel (Ni), palladium (Pd), ruthenium (Ru), rhodium (Rh), platinum (Pt), etc. Among these transition metals, iridium (Ir), nickel (Ni), palladium (Pd), ruthenium (Ru), rhodium (Rh), platinum (Pt), etc. are preferable.

The chiral ligands represented by L include bidentate ligands and monodentate ligands, more preferable ones being, for example, optically active ligands of phosphorus series such as optically active phosphine ligands, etc., optically active ligands of nitrogen series such as optically active bisoxazoline ligands, optically active diamine ligands, optically active bispyridine ligands, etc. Among them, optically active bidentate phosphine ligands, optically active bisoxazoline ligands, optically active diamime ligands, optically active bispyridine ligands, etc. are preferable.

Examples of the optically active ligands of phosphorus series include BINAP: 2,2'-bis(diphenylphosphino)-1,1'-binaphthyl, BINAP derivatives and other optically active bidentate phosphine ligands. The BINAP derivatives include BINAP derivatives which have either alkyl and aryl groups on the naphthyl rings of BINAP or BINAP derivatives which have 1 to 5, the same or different, alkyl groups (the same as those mentioned above) per one benzene ring binding to the phosphorus atom of BINAP as substituents. Specific examples of such BINAP derivatives include Tol-BINAP: 2,2'-bis(di-p-tolylphosphino)-1,1'-binaphthyl, xylyl-BINAP: 2,2'-bis[bis(3,5-dimethylphenyl)phosphino]-1,1'-binaphthyl, etc. Other specific examples of the optically active bidentate phosphine ligands include H8-BINAP: 2,2'-bis(diphenylphosphino)-5,6,7,8,5',6',7',8'-octahydro-1,1'-binaphthyl, BICHEP: 2,2'-bis(dicyclohexylphosphino)-6,6'-dimethyl-1,1'-binaphthyl, BPPFA: 1,2-bis(diphenylphosphino)-1-(N,N-dimethylaminoethyl)-ferrocene, CHIRAPHOS: 2,3-bis-(diphenylphosphino)butane, CYCPHOS: 1-cyclohexyl-1,2-bis-(diphenylphosphino)ethane, DEGPHOS: 1-substituted-3,4-bis-(diphenylphosphino)pyrrolidine, DIOP: 2,3-O-isopropylidene-2,3-dihydroxy-1,4-bis-(diphenylphosphino)butane, DIPAMP: 1,2-bis[(O-methoxyphenyl)phenylphosphino]ethane, Delphos: (substituted-1,2-bis(phosphorano)benzene), NORPHOS: 5,6-bis(diphenylphosphino)-2-norbornene, PNNP: N,N'-bis(diphenylphosphino)-N,N'-bis(1-phenyl)ethylenediamine, PROPHOS: 1,2-bis(diphenylphosphino)propane, SKEWPHOS: 2,4-bis(diphenylphosphino)pentane, SEGPHOS: (4,4'-bi-1,3-benzodioxiol)-5,5'-diylbis(diphenylphosphine), DM-SEGPHOS: (4,4'-bi-1,3-benzodioxiol)-5,5'-diylbis(di(3,5-dimethylphenyl)phosphine), DTBM-SEGPHOS: (4,4'-bi-1,3-benzodioxiol)-5,5'-diylbis(di(3,5-di-t-butyl-4-methoxyphenyl)phosphine), etc.

As the substituent groups in the substitutions mentioned above, there are conveniently adopted those of compounds well-known as known ligands in this field of technology.

Examples of the optically active bisoxazoline ligands include 2,2'-bis[4-tert-butyloxazol-2-yl]-1,1'-binaphthyl, 2,2'-bis[4-isopropyloxazol-2-yl]-1,1'-binaphthyl, 2,2'-bis[4-phenyloxazol-2-yl]-1,1'-binaphthyl, 2,2'-bis[4-benzyloxazol-2-yl]-1,1'-binaphthyl, 2,2'-bis[2-(4-phenyl-1,3-oxazolinyl)]propane, DBFOX: 4,6-dibenzofurandiyl-2,2'-bis(4-phenyloxazoline), 2,2'-isopropylidenebis(4-phenyloxazoline), 2,2'-isopropylidenebis(4-tert-butyloxazoline), etc.

Examples of the optically active diamine ligands include DPEN: 1,2-diphenyl-ethane-1,2-diamine, DAIPEN: 3-methyl-1,1-diphenyl-butane-1,2-diamine, N-(4-t-butylbenzenesulfonyl)-1,2-diphenylethylenediamine, etc.

Examples of the optically active ligands of nitrogen series include optically active bispyridine ligands such as BDPTZ: 1,4-bis(2,2'-dipyridylmethyl)-phthalazine, BPAN: 2,7-bis[2-(2-pyridylethyl)aminomethyl]-1,8-naphthyridine, TERPY: 2,2':6',2"-terpyridine, N,N-bis[2-(2-pyridyl)ethyl]-2-phenylethylamine, etc.

Examples of the counter anions represented by $Z^-$ include, not being limited to the counter anions mentioned above, but covering anionic ligands widely, for example, $H^-$, $OH^-$, $[OR']^-$, $[R'HN]^-$, $[R'_2N]^-$, $H_2N^-$, $[R'_3SiO]^-$, $F^-$, $Br^-$, $Cl^-$, $I^-$, $I_3^-$, $NH_2CO^-CO^-$, $CH_3COO^-$, $CF_3COO^-$, $CF_3CF_2COO^-$, $CF_3CF_2CF_2COO^-$, $CF_3SO_3^-$, p-$CH_3C_6H_4SO_3^-$, $ClO_4^-$, $NO_3^-$, $SO_4^{2-}$, $CO_3^{2-}$, $PO_4^-$, $B(C_6H_5)_4^-$, $B[3,5-(CF_3)_2C_6H_3]_3^-$, $PF_6^-$, $SbF_6^-$, $AsF_6^-$, $(CH_3COCHCOCH_3)^-$, etc. In the anionic ligands, monovalent anionic ligands are preferable. Here, R' represents, the same or different, an alkyl group which may be substituted, a heteroalkyl group which may be substituted, a cycloalkyl group which may be substituted, an aryl group which may be substituted, a heterocyclic group which may be substituted, an aralkyl group which may be substituted, a heteroaralkyl group which may be substituted, etc. The heteroalkyl groups mean alkyl groups substituted with heterocyclic groups as described above for $R^1$ and $R^2$, the substituent group of which are appropriately selected from the substituent groups described above for the formula (1). The cycloalkyl has the same meanings as the cyclic alkyl group described above for $R^1$ to $R^3$. The heteroaralkyl groups mean aralkyl groups substituted with the heterocyclic groups described above for $R^1$ to $R^3$. It goes without saying that the alkyl groups, aryl groups and aralkyl groups may be the same as those described above.

Examples of the neutral ligands represented by B include aromatic compounds, olefinic compounds and compounds which can act as neutral ligands (hereinafter called other neutral ligands). Examples of the aromatic compounds include benzonitrile and alkyl-substituted benzenes. Examples of the alkyl-substituted benzenes include, for example, p-cymene(p-Cymene), hexamethylbenzene, 1,3,5-trimethylbenzene(mesitylene), etc. Examples of the olefinic compounds include ethylene, 1,5-cyclooctadiene, cyclopentadiene, pentamethylcyclopentadiene, norbornadiene, etc. Examples of other neutral ligands include N,N-dimethylformamide (DMF), acetonitrile, acetone, chloroform, etc.

Various known complexes described below may be used as the chiral transition metal complexes mentioned above in the present invention. Such known complexes include those which consist of the cationic moiety [MLrBs] constructed with transition metals, chiral ligands and anionic ligands and the counter anion ($Z^-$), and those in which substances having a high coordination properties are directly bound to the transition metals as in, for example, the acetate complexes, trifluoroacetate complexes, triflate complexes, and acetylacetonato complexes, etc.

As the chiral metal complexes represented by the above formulae (5) and (6), the chiral metal complexes described below, for example, are preferable.

When M is Pd and L is a monodentate chiral ligand, then p=4, q=y=2, r=c=2, s=0 or 2, and when L is a bidentate ligand, then p=q=y=2, r=1, c=2, s=0 or 2.

When M is Ni and L is a monodentate chiral ligand, then r=c=2, s=0, 2, 4 or 6, and when L is a bidentate ligand, then r=1, c=2, s=0, 4 or 6.

Furthermore, L may be ligands other than mono- or bidentate ligands, including, for example, tri- or hexadentate ligands. In the latter cases, the chiral transition metal complexes which may be used in the present invention can be represented by the formula (7):

$[Ni_eL_pA_qH_f]_y^+(Z^-)_y$ (7)

wherein e is 2 or 4; p is 1, 2 or 4; q is 1 or 2; f is an integer of 1 to 4; y is an integer of 2 to 4; and A and $Z^-$ have each the same meanings as described above.

When M is Pt and L is a monodentate chiral ligand, then p=4, q=y=2, r=c=2, s=0, and when L is a bidentate chiral ligand, then r=1, c=2, s=0, p=q=y=2. Furthermore, in some Pt complexes, wherein M is Pt, there exists a type of Pt complexes in which one of the counter anions is bound directly to Pt and the other one exists as a counter anion. In these complexes, when L is a monodentate ligand, then r=c=2 and s=1, and when L is a bidentate ligand, then c=2 and r=s=1. This type of complexes, where one of the counter anions is bound directly to the transition metal, and the other one exists as the counter anion, are not limited to Pt complexes, but known in various chiral transition metal complexes as those of Rh, Pd, etc., as described below, and also contained in the chiral transition metal complexes which may be used in the present invention.

When M is Ir or Rh and L is a monodentate chiral ligand, then r=2, s=c=1, p=4, q=2 and y=0, and when L is a bidentate chiral ligand, then r=s=c=1, p=q=2 and Y=0.

When M is Ru, cases (i) to (iv) which follow are preferable: (i) A is $Cl^-$, $Br^-$ or $I^-$, B is a neutral ligand such as an aromatic compound or an olefinic compound, etc., $Z^-$ is $Cl^-$, $Br^-$, $I^-$, $I_3^-$, $CF_3SO_3^-$, p-$CH_3C_6H_4SO_3^-$, etc., and when L is a monodentate chiral ligand, then s=1, r=2 and c=0 or 2, and when L is a bidentate chiral ligand, then c=2 or 0 and s=r=1. (ii) $Z^-$ is $BF_4^-$, $ClO_4^-$, $OTf^-$, $PF_6^-$, $SbF_6^-$, $BPh_4^-$, etc., and when L is a monodentate chiral ligand, then r=c=2 and s=0, and when L is a bidentate chiral ligand, then r=1, s=0 and c=2. (iii) Z is H (hydrogen atom), and when L is a monodentate chiral ligand, then c=2 and r=4, and when L is a bidentate ligand, then c=r=2. (iv) Z is H or CO, and when L is a monodentate chiral ligand, then c=r=2, and when L is a bidentate chiral ligand, then c=2 and r=1.

When M is Fe, the cases (i) and (ii) which follow are preferable: (i) B is a neutral ligand such as an aromatic compound, olefinic compound, etc., and when L is a bidentate chiral ligand, then c=s=r=1, and when L is a monodentate chiral ligand, then c=s=1 and r=2, (ii) when L is a bidentate chiral ligand, then c=3, s=0 or 6 and r=1, and when L is a monodentate chiral ligand, then c=3, s=0 or 6 and r=2.

When M is Co, the cases (i) and (ii) below are preferable: (i) B is a neutral ligand such as an aromatic compound, an olefinic compound, etc., and when L is a bidentate chiral ligand, then c=0 and s=r=1, and when L is a monodentate chiral ligand, then c=0, s=1 and r=2, (ii) L is a bidentate chiral ligand, then c=2, s=0 and r=1, and when L is a monodentate chiral ligand, then c=r=2 and s=0.

When M is Cu, the cases (i) and (ii) below are preferable: (i) when Cu is divalent and L is a monodentate chiral ligand, then p=4, q=y=2, r=c=2 and s=0 or 1, and when L is a bidentate chiral ligand, then p=q=y=2, r=1, c=2 and s=1, (ii) when Cu is monovalent, and when L is a bidentate chiral ligand, then s=0 and r=c=1, and when L is a monodentate chiral ligand, then s=0, c=1 and r=2.

When M is Ag or Au, in cases where L is a bidentate chiral ligand, then r=c=1 and s=0 or 1, and where L is a monodentate chiral ligand, then r=2, c=1 and s=0 or 1.

Further, when M is Ir or Rh, preferable complexes are those in which B is 1,5-cyclooctadiene or norbornadiene, and Z is $BF_4$, $ClO_4$, OTf, $PF_6$, $SbF_6$, OH, $BPh_4$, etc.

The following is the more specific description about the chiral transition metal complexes represented by the above formulae (5) and (6). In addition, symbols used in the formulae of transition metal complexes below have the meanings as follows: L: a chiral ligand; cpd: cyclopentadiene, cod: 1,5-cyclooctadiene; nbd: norbornadiene; OTf: a triflate group ($SO_2CF_3$); Ph: a phenyl group, Ac: an acetyl group, acac: an acetylacetonato group, OTs: a p-toluenesulfonate group, p-cymene: para-1-cymene, Cp*: a pentamethylcyclopentadiene group. Although specific examples of the transition metal complexes given below are selected principally from those which have bidentate ligands as the chiral ligand to avoid too much complexity for the explanation, the chiral transition metal complexes used in the present invention are not limited to those exemplified below.

Rhodium Complexes:

Rhodium complexes can be prepared, for example, by the methods described in Jikken-Kagaku-Kouza, 4$^{th}$ Ed., Vol. 18, Organic Metal Complexes, p. 339-344 (1991) (Edited by Nihon Kagakukai) (Maruzen) or according to the methods described in the literature, J. Am. Chem. Soc., 2002, 5052, etc. To be more specific, such rhodium complexes can be prepared by reacting bis(cycloocta-1,5-diene)rhodium(I) tetrafluoroborate with a chiral ligand.

Specific examples of the rhodium complexes include, for example, those below:

[Rh(L)Cl]$_2$, [Rh(L)Br]$_2$, [Rh(L)I]$_2$, [Rh(L)(μ-OH)]$_2$, [Rh(cod)(L)](BF$_4$), [Rh(cod)(L)](ClO$_4$), [Rh(L)CP*]$_2$, [Rh(cod)(L)]PF$_6$, [Rh(cod)(L)]BPh$_4$, [Rh(cod)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, and [Rh(nbd)(L)]OTf.

Ruthenium Complexes:

Ruthenium complexes can be prepared by the methods described in the literature: J. Chem. Soc., Chem. Commun., 1985, 922, etc. More specifically, they can be prepared by heating [Ru(cod)Cl$_2$]$_n$ and a chiral ligand in toluene under reflux in the presence of triethylamine.

They can also be prepared by the method described in the literature: J. Chem. Soc., Chem. Commun., 1989, 1208, etc. More specifically, they can be prepared by heating [Ru(p-cymene)I]$_2$ and a chiral ligand in methylene chloride and ethanol with stirring.

Specific examples of the ruthenium complexes include those below:

Ru(OAc)$_2$(L), Ru$_2$Cl$_4$(L)$_2$NEt$_3$, RuH$_2$(L)$_2$, RuH(CO)(L), [Ru(p-cymene)(L)], [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$.

Iridium Complexes:

Iridium complexes can be prepared by the methods described in the literature: J. Organomet. Chem., 1992, 428, 213; J. Am. Chem. Soc., 1997, 10857, etc. More specifically, they can be prepared by reacting a chiral ligand with [Ir(cod)(CH$_3$CN)$_2$]BF$_4$ in tetrahydrofuran with stirring.

Specific examples of the iridium complexes include those below:

[Ir(L)Cl]$_2$, [Ir(L)Br]$_2$, [Ir(L)I]$_2$, [Ir(L)(μ-OH)]$_2$, [Ir(L(Cp*)]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$ and [Ir(nbd)(L)]OTf.

Palladium Complexes:

Palladium complexes prepared by the methods described in the literature: J. Am. Chem. Soc., 1999, 5450, etc., can be used after isolation. Specific examples of the palladium complexes include those below:

PdCl$_2$(L), [Pd(L)](BF$_4$)$_2$, [Pd(L)](ClO$_4$)$_2$, [Pd(L)](PF$_6$)$_2$, [Pd(L)](BPh$_4$)$_2$, [Pd(L)](OTf)$_2$, [Pd(L)(acac)](OTf), [Pd(L)(H$_2$O)$_2$](BF$_4$)$_2$, [Pd(L)(H$_2$O)$_2$](ClO$_4$)$_2$, [Pd(L)(H$_2$O)$_2$](PF$_6$)$_2$, [Pd(L)(H$_2$O)$_2$](BPh$_4$)$_2$, [Pd(L)(H$_2$O)$_2$](OTf)$_2$, [{Pd(L)(μ-OH)}$_2$](BF$_4$)$_2$, [{Pd(L)(μ-OH)}$_2$](ClO$_4$)$_2$, [{Pd(L)(μ-OH)}$_2$](PF$_6$)$_2$, [{Pd(L)(μ-OH)}$_2$](BPh$_4$)$_2$, [{Pd(L)(μ-OH)}$_2$](ClO$_4$)$_2$ and [{Pd(L)(μ-OH)}$_2$](OTf)$_2$.

Nickel Complexes:

Nickel complexes can be prepared by the methods described in Jikken-Kagaku-Kouza, 4$^{th}$ Ed., Vol. 18, Organic Metal Complexes, p. 376 (1991) (Edited by Nihon Kagakukai) (Maruzen), and in the literature, for example, J. Am. Chem. Soc., 1991, 113, 9887; J. Am. Chem. Soc., 2001, 123, 11168-11178; J. Am. Chem. Soc., 2000, 122, 184-185; J. Am. Chem. Soc., 1998, 120, 10567-10568 and J. Am. Chem. Soc., 1999, 121, 11751-11757, etc., or more specifically, by dissolving a chiral ligand and nickel chloride in a mixed solvent of 2-propanol and methanol, followed by heating with stirring.

Specific examples of the nickel complexes include those below:

NiCl$_2$(L), NiBr$_2$(L), NiI$_2$(L), Ni(OAc)$_2$(L)(H$_2$O)$_4$, Ni(Cl)$_2$(L)(H$_2$O)$_6$, Ni(OAc)$_2$(L), [Ni(acac)(L)](OTf), [Ni(L)(H$_2$O)$_2$](ClO$_4$)$_2$, [Ni$_2$(L)(OAc)$_2$(H$_2$O)](ClO$_4$)$_2$, [{Ni(L)(μ-OH)}$_2$(H$_2$O)](ClO$_4$)$_2$, [Ni$_2$(L)(H$_2$O)$_4$](OTs)$_4$, [Ni$_2$(L)(μ-OH)(H$_2$O)$_3$](OTs)$_3$, [Ni$_2$(L)(μ-OH)$_2$(H$_2$O)]$_4$(OTs)$_4$.

Platinum Complexes:

Platinum complexes can be manufactured by the methods described in Jikken-Kagaku-Kouza, 4$^{th}$ Ed., Vol. 18, Organic Metal Complexes, p. 412 (1991) (Edited by Nihon Kagakukai) (Maruzen), and in the literature, for example, Organometallics, 1995, 5281; J. Chem. Soc. Dalton, trans., 1989, 403 and J. Am. Chem. Soc., 1998, 10032, etc. Specific examples of the platinum complexes include, for example, those below:

PtCl$_2$(L), PtBr$_2$(L), PtI$_2$(L), [Pt(μ-OH)(L)]$_2$(NO$_3$)$_2$, [Pt(μ-OH)(L)]$_2$(ClO$_4$)$_2$, Pt(OH)$_2$(L), [Pt(L)(H$_2$O)(OTf)](OTf), [Pt(L)(H$_2$O)(OH)](OTf) and [Pt(acac)(L)](OTf).

Iron Complexes:

Iron complexes can be prepared by the methods described in Jikken-Kagaku-Kouza, 4$^{th}$ Ed., Vol. 18, Organic Metal Complexes, p. 212 (1991) (Edited by Nihon Kagakukai) (Maruzen), etc. Specific examples of the iron complexes include, for example, those below:

[Fe(cpd)(L)]Cl, [FeCl$_3$(L)](H$_2$O)$_6$ and [Fe(acac)$_3$(L)].

Cobalt Complexes:

Cobalt complexes can be prepared by the methods described in Jikken-Kagaku-Kouza, 4$^{th}$ Ed., Vol. 18, Organic Metal Complexes, p. 295 (1991) (Edited by Nihon Kagakukai) (Maruzen), etc. Specific examples of the cobalt complexes include those below:

[Co(cpd)(L)], [Co(OAc)$_2$(L)] and [Co(acac)$_2$(L)].

Gold Complexes:

Gold complexes can be prepared by the methods described in Jikken-Kagaku-Kouza, 4$^{th}$ Ed., Vol. 18, Organic Metal Complexes, p. 455 (1991) (Edited by Nihon Kagakukai) (Maruzen), etc. Specific examples of the gold complexes include, for example, a complex given below:

AuCl(L).

Silver Complexes:

Silver complexes can be prepared by the methods described in Jikken-Kagaku-Kouza, 4$^{th}$ Ed., Vol. 18, Organic Metal Complexes, p. 450 (1991) (Edited by Nihon Kagakukai) (Maruzen), etc. Specific examples of the silver complexes include, for example, a complex given below:

Ag(cpd)(L)(OTf).

Copper Complexes:

Copper complexes can be prepared by the methods described in Jikken-Kagaku-Kouza, 4$^{th}$ Ed., Vol. 18, Organic Metal Complexes, p. 440 (1991) (Edited by Nihon Kagakukai) (Maruzen), or according to the methods described in the literature: Inorg. Chem., 1965, 1382, etc. Specific examples of the copper complexes include those below:

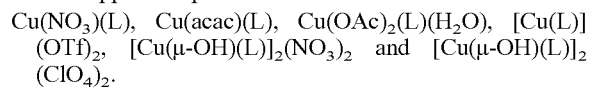

In the above description of the organic metal complexes, L has the same meaning as mentioned above, and Ac, Ph, Ts and Tf represent acetyl, phenyl, tosyl and triflate groups, respectively.

These chiral transition metal complexes used in the present invention can be prepared, as described above, by using the known methods. In particular, they can be prepared by the ligand-exchange methods (the methods to obtain the complexes with a desired anion ligand or a counter-anion by exchanging the ligand from a weakly neutral ligand to a chiral phosphine one or a chiral nitrogen one, or by treating a halogeno ligand with a silver salt). Since these methods have already been established so well, they can be appropriately used also in the present invention.

Furthermore, there are other known production methods of the chiral transition metal complex catalysts such as those described in J. Am. Chem. Soc., 121, 5450 (1999) and J. Org. Chem., 60, 2648 (1995), etc., and the complexes prepared and isolated by these methods can also be used. In these cases, the complexes obtained may be used as the chiral transition metal complexes employable in the present invention both after purification and without particular purification. It is also possible to carry out the production method of the present invention, wherein starting materials for the preparation of the complexes are added to the reaction system (in situ).

The production method of the present invention may be carried out in the presence of an acid, when a free amine (amines when a=0 in the above formula (3)) is used as the amine. However, it is not necessary to carry out the production method of the present invention in the presence of an acid in cases where amine acid salts (amines a=1 in Formula (3) above) are used, but it is enough to carry out the reaction in the presence of an acid in accordance with the necessity.

Examples of the acids include inorganic acids, organic acids and Lewis acids, etc. Examples of the inorganic acids include, for example, hydrochloric acid, hydrobromic acid, sulfuric acid, phosphoric acid, tetrafluoroboric acid, perchloric acid, periodic acid, etc., and examples of the organic acids include, for example, carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, glycolic acid, etc., and sulfonic acids such as methanesulfonic acid, benzenesulfonic acid, p-toluenesulfonic acid, trifluoromethanesulfonic acid, etc. Examples of the Lewis acids include, for example, aluminum halogenides such as aluminum chloride, aluminum bromide, etc.; dialkylaluminum halogenides such as diethylaluminum chloride, diethylaluminum bromide, diisopropylaluminum chloride, etc.; trialkoxyaluminums such as triethoxyaluminum, triisopropoxyaluminum, tri-tert-butoxyaluminum, etc.; titanium halogenides such as titanium tetrachloride, etc.; tetraalkoxytitaniums such as tetraisopropoxytitanium, etc.; boron halogenides such as boron trifluoride, boron trichloride, boron tribromide, boron trifluoride diethyl ether complex, etc.; and zinc halogenides such as zinc chloride, zinc bromide, etc.

Each of these acid may be used alone or appropriately in combination of two kinds of them may be used. Among the acids mentioned above, methanesulfonic acid, trifluoromethanesulfonic acid, etc. are especially preferable.

The amount of the acid used may be appropriately selected from the range of usually about 0.1 to 10 equivalents, or more preferably about 0.5 to 3 equivalents to that of the amine.

In the production method of the present invention, the amount of the amines used represented by the formula (3) may be appropriately selected from the range of usually about 0.5 to 10 equivalents, or more preferably about 1.0 to 3 equivalents to that of the α,β-unsaturated carboxylic acid derivative represented by the formula (1).

The amount of the chiral catalyst used may be appropriately selected from the range of usually about 0.0001 to 1.0 equivalent, or more preferably about 0.001 to 0.1 equivalent to that of the compound (1).

The production method of the present invention may be carried out in a solvent, if necessary. Examples of the solvent include, for example, aliphatic hydrocarbons such as pentane, hexane, heptane, octane, decane, cyclohexane, etc.; aromatic hydrocarbons such as benzene, toluene, xylene, etc.; halogenated hydrocarbons such as dichloromethane, 1,2-dichloroethane, chloroform, carbon tetrachloride, o-dichlorobenzene, etc.; ethers such as diethyl ether, diisopropyl ether, tert-butyl methyl ether, dimethoxyethane, ethyleneglycol diethyl ether, tetrahydrofuran, 1,4-dioxane, 1,3-dioxolane, etc.; ketones such as acetone, methyl ethyl ketone, methyl isobutyl ketone, cyclohexanone, etc.; alcohols such as methanol, ethanol, 2-propanol, n-butanol, 2-ethoxyethanol, benzyl alcohol, etc.; polyalcohols such as ethylene glycol, propylene glycol, 1,2-propanediol, glycerol, etc.; esters such as methyl acetate, ethyl acetate, n-butyl acetate, methyl propionate, etc., amides such as formamide, N,N-dimethylformamide, N,N-dimethylacetamide, etc.; sulfoxides such as dimethylsulfoxide, etc.; cyano-containing organic compounds such as acetonitrile, etc.; N-methylpyrrolidone; water; etc. Each of these solvents may be used alone or appropriately in combination of two kinds of them.

The amount of the solvent used is appropriately selected usually from the range of about 0.5 to 100 equivalents, or more preferably from the range of 1 to 10 equivalents to the amount of the compound (1).

The production method of the present invention may be carried out, if necessary, under atmosphere of inert gases. Examples of the inert gases include nitrogen, argon, etc.

The reaction temperature is appropriately selected usually from a range of about −70 to 200° C., or more preferably of a range of about 0 to 100° C.

The reaction time is appropriately selected usually from the range of about 0.5 hours to 100 hours, or more preferably from the range of about 0.5 hours to 24 hours.

The optically active β-amino acid derivatives thus obtained can be converted to N-substituted-β-amino acids, for example, by hydrolysis.

Both the starting materials used in the present invention and the objective compounds may be either in the form of free acids or bases, or in the form of their salts with bases when the materials and compounds are acids, or with acids, when they are acids. Examples of the acids which can form salts include the acids, represented by X above, such as hydrochloric acid, sulfuric acid, acetic acid, citric acid, etc., and examples of the bases which can form salts include inorganic and organic bases such as sodium hydroxide, potassium hydroxide, ammonia, dimethylamine, diethylamine, isopropylamine, etc.

The optically active β-amino acid derivatives represented by the above formula (2) and obtainable by the production method of the present invention have reactive groups such as $COR^4$, NH, etc., in the molecule and are therefore useful, for example, as intermediates for the synthesis of medicines, agricultural chemicals, etc. Furthermore, according to the present invention, an optically active β-amino acid derivative can be obtained in good yield and with optical purities even in a reaction with a primary amine having a group, such as methoxyphenyl, which may be removed afterwards in a deprotecting step to give a free β-amino acid derivative.

Furthermore, although it has been difficult, until now, to prepare β-amino acid derivatives of high optical purities in the reaction with anisidine in the presence of conventional catalysts, the method of the present invention has made it possible to obtain optically active β-amino acid derivatives in high yields and optical purities even in the reaction with anisidine, because such optically active β-amino acid derivatives obtained by the method of the present invention can be converted into free β-amino acid derivatives.

The optically active β-amino acid derivatives of the above formula (4), for example, the above formulae (4a) and (4c) are therefore useful as intermediates for the synthesis of, for example, medicines, agricultural chemicals, etc.

According to the present invention, β-amino acid derivatives can be obtained using amines as starting materials and without going through the process of deprotection. Therefore, the present invention has the effect to improve the workability of the previous methods and make it possible to produce the desired β-amino acid derivatives economically.

Hitherto, it has been difficult to obtain the desired β-amino acid derivatives in good optical purities in the reaction of primary amines substituted with, in particular, halogenated hydrocarbon groups such as trifluoromethyl, with α,β-unsaturated carboxylic acid derivatives in the presence of chiral catalysts. The present invention has its prominent effectiveness in that it has solved the problem mentioned above, giving the desired β-amino acids having halogenated hydrocarbon substituents in good optical purities.

Furthermore, according to the present invention, optically active β-amino acid derivatives can be obtained in an extremely high chemical and optical yields, even in the reaction with primary amines carrying a group, such as methoxyphenyl, which may be removed in a deprotection step to give free β-amino acid derivatives.

In addition, the production method of the present invention requires only catalytic amount of chiral catalyst.

BEST MODE FOR CARRYING OUT THE INVENTION

The present invention will be described in more detail referring to Examples and Comparison Examples, but it is in no way restricted to these Examples.

The apparatus used for measuring physical properties, etc. in Examples below is as follows:

(1) Nuclear Magnetic Resonance Spectrum: DRX 500 (BRUKER JAPAN Co. Ltd.), $^1$H-NMR (500.13 MHz), $^{13}$C-NMR (125.76 MHz)

(2) Gas chromatography (GLC): Hewlett Packard 5890-II (3) High Performance Liquid Chromatography (HPLC): Shimadzu LC10AT & SPD 10A

EXAMPLE 1

To a solution of 4-trifluoromethylaniline (121 mg, 0.75 mmol) and methyl 2-pentenoylcarbamate (79 mg, 0.5 mmol) in toluene (2 ml) in a stream of nitrogen was added Pd((R)-binap)(H$_2$O)$_2$(OTf)$_2$ (13.3 mg, 0.0125 mmol) and the resulting mixture was stirred at 50° C. for 5 hours. After completion of the reaction, the reaction mixture was concentrated and the residue was purified by a silica gel column chromatography (hexane:ethyl acetate=3:1 to 1:1) to give the objective compound methyl 3-(4-trifluoromethylanilino) pentanoylcarbamate (143 mg, 45% yield). Enantiomeric excess ratio of this product was determined by a liquid chromatography using a column for separation of optical isomers (column: OJ-R) to be 59% e.e. (S form).

EXAMPLE 2

To a solution of 4-trifluoromethylaniline (121 mg, 0.75 mmol) and methyl 2-pentenoylcarbamate (79 mg, 0.5 mmol) in toluene (2 ml) in a stream of nitrogen was added Pd((S)-dm-binap)(H$_2$O)$_2$(OTf)$_2$ (14.7 mg, 0.0125 mmol) and the resulting mixture was stirred at 50° C. for 5 hours. After completion of the reaction, the reaction mixture was concentrated and the residue was purified by a silica gel column chromatography (hexane:ethyl acetate=3:1 to 1:1) to give the objective compound methyl 3-(4-trifluoromethylanilino) pentanoylcarbamate (159 mg, 50% yield). Enantiomeric excess ratio of this product was determined by a liquid chromatography using a column for separation of optical isomers (column: OJ-R) to be 61% e.e. (R form).

EXAMPLE 3

To a solution of 4-trifluoromethylaniline (193 mg, 1.2 mmol) and 3-crotonoyl-1,3-oxazolidin-2-one (155 mg, 1.0 mmol) in toluene (3 ml) in a stream of nitrogen was added Pd((R)-binap)(H$_2$O)$_2$(OTf)$_2$ (26.6 mg, 0.025 mmol) and the resulting mixture was stirred at room temperature for 16 hours. After completion of the reaction, a saturated aqueous solution of ammonium chloride (10 ml) was added to the reaction mixture and the resulting mixture was extracted with ethyl acetate (10 ml). The organic layer was dried over anhydrous magnesium sulfate. The solvent was then evaporated off and the crude product obtained was purified by a silica gel column chromatography (hexane:ethyl acetate=1:1) to give the objective compound 3-(4-trifluoromethylanilino)butyryl-1,3-oxazolidin-2-one (238 mg, 75% yield). Enantiomeric excess ratio of this product was determined by a liquid chromatography using a column for separation of optical isomers (column: AD-H) to be 83% e.e.

EXAMPLE 4

To a solution of 4-trifluoromethylaniline (193 mg, 1.2 mmol) and 3-crotonoyl-1,3-oxazolidin-2-one (155 mg, 1.0 mmol) in toluene (3 ml) in a stream of nitrogen was added Pd((R)-segphos)(H$_2$O)$_2$(OTf)$_2$ (26.3 mg, 0.025 mmol) and the resulting mixture was stirred at room temperature for 14 hours. After completion of the reaction, a saturated aqueous solution of ammonium chloride (10 ml) was added to the reaction mixture and the resulting mixture was extracted with ethyl acetate (10 ml). The organic layer was dried over anhydrous magnesium sulfate. The solvent was then evaporated off and the crude product obtained was purified by a silica gel column chromatography (hexane:ethyl acetate=1:1) to give the objective compound 3-(4-trifluoromethylanilino)butyryl-1,3-oxazolidin-2-one (238 mg, 75% yield). Enantiomeric excess ratio of this product was determined by a liquid chromatography using a column for separation of optical isomers (column: AD-H) to be 84% e.e.

EXAMPLE 5

To a solution of 4-trifluoromethylaniline (193 mg, 1.2 mmol) and 3-(2-pentenoyl)-1,3-oxazolidin-2-one (189 mg, 1.0 mmol) in toluene (3 ml) in a stream of nitrogen was added Pd((R)-binap)(H$_2$O)$_2$(OTf)$_2$ (26.6 mg, 0.025 mmol), and the resulting mixture was stirred at room temperature for 16 hours. After completion of the reaction, a saturated aqueous solution of ammonium chloride (10 ml) was added to the reaction mixture and the mixture was extracted with ethyl acetate (10 ml). The organic layer was dried over anhydrous magnesium sulfate. The solvent was then evaporated off and the crude product obtained was purified by a silica gel column chromatography (hexane:ethyl acetate=1:1) to give the objective compound 3-[3-(4-trifluoromethylanilino)pentanoyl]-1,3-oxazolidin-2-one (165 mg, 50% yield). Enantiomeric excess ratio of this product was determined by a liquid chromatography using a column for separation of optical isomers (column: OA-2000) to be 70% e.e.

EXAMPLE 6

To a solution of 3-crotonoyl-1,3-oxazolidin-2-one (155 mg, 1.0 mmol) in toluene (3 ml) in a stream of nitrogen was added Pd((R)-binap)(H$_2$O)$_2$(OTf)$_2$ (26.6 mg, 0.025 mmol), and the resulting mixture was cooled to 0° C. Aniline (0.11 ml, 1.2 mmol) was added to the mixture, and to the solution was added slowly methanesulfonic acid (0.039 ml, 0.6 mmol). Then, the cooling ice-bath was removed and the reaction mixture was reacted at room temperature for 15 hours with stirring. After completion of the reaction, the solvent was evaporated off, and the crude product obtained was purified by a silica gel column chromatography (hexane:ethyl acetate=1:1) to give the objective compound 3-(3-phenylaminobutyryl)-oxazolidin-2-one (58 mg, 23% yield). Enantiomeric excess ratio of this product was determined by a liquid chromatography using a column for separation of optical isomers (column: AD-H) to be 78% e.e.

EXAMPLE 7

To a solution of 3-crotonoyl-1,3-oxazolidin-2-one (155 mg, 1.0 mmol) in ethyl acetate (3 ml) in a stream of nitrogen was added Pd((R)-binap)(H$_2$O)$_2$(OTf)$_2$ (26.6 mg, 0.025 mmol), and the resulting mixture was cooled to 0° C. Aniline (0.11 ml, 1.2 mmol) was added to the mixture, and to the solution was added slowly methanesulfonic acid (0.078 ml, 1.2 mmol). Then, the cooling ice-bath was removed and the reaction mixture was reacted at room temperature for 18 hours with stirring. After completion of the reaction, the solvent was evaporated off, and the crude product obtained was purified by a silica gel column chromatography (hexane:ethyl acetate=1:1) to give the objective compound 3-(3-phenylaminobutyryl)-oxazolidin-2-one (37 mg, 15% yield). Enantiomeric excess ratio of this product was determined by a liquid chromatography using a column for separation of optical isomers (column: AD-H) to be 82% e.e.

EXAMPLE 8

A solution of anisidine (55.4 mg, 0.45 mmol) in toluene (1.5 ml) was cooled to 0° C., and trifluoromethanesulfonic acid (40 µL, 0.45 mmol) was added dropwise. The mixture was stirred for 10 minutes, and to this solution were added Pd((R)-binap)(OH$_2$)$_2$(OTf)$_2$ (8 mg, 0.00752 mmol) and 3-crotonoyl-1,3-oxazolidin-2-one (47 mg, 0.3 mmol). The ice-cooling bath was removed and the mixture was reacted at room temperature for 20 hours. A saturated aqueous solution of ammonium chloride was added to quench the reaction, and the reaction mixture was extracted with ethyl acetate. The organic layer was concentrated and purified by a silica gel column chromatography (hexane:ethyl acetate=4:1) to give the objective 3-[3-(4-methoxyphenylamino)butyryl]-1,3-oxazolidin-2-one (66.5 mg, 96% yield). The enantiomeric excess was determined by a liquid chromatography with an optical isomer separating column (column: AD-H) to be 94% e.e.

EXAMPLE 9

To a solution of Pd((R)-binap)(OH$_2$)$_2$(OTf)$_2$ (26.6 mg, 0.025 mmol) in toluene (3 ml) were added 3-crotonoyl-1,3-oxazolidin-2-one (155 mg, 1.0 mmol) and anisidine (148 mg, 1.2 mmol). After the resulting mixture was stirred at room temperature for 3 hours, the reaction solution was concentrated and purified by a silica gel column chromatography (hexane:ethyl acetate=4:1) to give the objective 3-[3-(4-methoxyphenylamino)butyryl]-1,3-oxazolidin-2-one (228 mg, 82% yield).

EXAMPLE 10

A solution of 3-crotonoyl-1,3-oxazolidin-2-one (47 mg, 0.3 mmol) and Pd((R)-binap)(H$_2$O)$_2$(OTf)$_2$ (8.0 mg, 0.0075 mmol) in toluene (1.5 ml) in a stream of nitrogen was cooled to 0° C., and aniline (42 mg, 0.45 mmol) was added. To the solution was dropwise added trifluoromethanesulfonic acid (63 µL, 0.45 mmol), and the resulting mixture was stirred at room temperature for 24 hours. When no starting material was detected, a saturated aqueous solution of ammonium chloride was added to quench the reaction, and the resulting mixture was extracted with ethyl acetate. The organic layer was concentrated and purified by a silica gel column chromatography (hexane:ethyl acetate=1:1) to give the objective 3-(3-phenylaminobutyryl)-oxazolidin-2-one (66 mg, 89% yield). The enantiomeric excess ratio was determined to be 94%. e.e. by a liquid chromatography with an optical isomer separating column (column: AD-H).

EXAMPLE 11

In a stream of nitrogen, a solution of 3-crotonoyl-1,3-oxazolidin-2-one (776 mg, 5.0 mmol), anisidine trifluoromethanesulfonate (1.64 g, 6.0 mmol), anisidine (3.1 mg, 0.005 mmol) and Pd((R)-segphos)(H$_2$O)$_2$(OTf)$_2$ (26.3 mg, 0.005 mmol) in tetrahydrofuran (5 ml) was stirred at room temperatures for 24 hours. When no starting material remained was noticed, a saturated aqueous solution of ammonium chloride was added to quench the reaction and the resulting mixture was extracted with ethyl acetate. The organic layer was concentrated and purified by a silica gel column chromatography (hexane: ethyl acetate=1:1) to give the objective 3-[3-(4-methoxyphenylamino)butyryl]-1,3-oxazolidin-2-one (1.16 g, in a yield of 83%). The enantiomeric excess ratio was determined to be 97% e.e. by a liquid chromatography with an optical isomer separating column (column: AD-H).

In the description above, Me and HOTf mean a methyl group and trifluoromethanesulfonic acid, respectively. Hereinafter the same shall be applied.

EXAMPLE 12

In a stream of nitrogen, a solution of 3-crotonoyl-1,3-oxazolidin-2-one (78 mg, 0.5 mmol), anisidine trifluoromethanesulfonate (205 mg, 0.75 mmol) and Pd((R)-binap)(μ-OH)]$_2$(OTf)$_2$ (4.6 mg, 0.0025 mmol) in tetrahydrofuran (0.5 mL) was stirred at room temperatures for 12 hours. When no starting material remained was observed, a saturated aqueous solution of ammonium chloride was added to quench the reaction, and the resulting mixture was extracted with ethyl acetate. The organic layer was concentrated and purified by a silica gel column chromatography (hexane:ethyl acetate=1:1) to give the objective 3-[3-(4-methoxyphenylamino)butyryl]-1,3-oxazolidin-2-one (128 mg, 92% yield). The enantiomeric excess ratio was determined to be 98% e.e. by a liquid chromatography with an optical isomer separating column (column: AD-H).

INDUSTRIAL APPLICABILITY

The optically active β-amino acid derivatives obtainable by the production method of the present invention are useful as intermediates for, for example, medicines, agricultural chemicals, etc.

The invention claimed is:

1. A process for producing an optically active β-amino acid derivative of the formula (2):

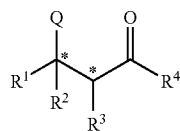

(2)

wherein $R^1$ and $R^2$ are each independently a hydrogen atom, a hydrocarbon group which may be substituted, an acyl group which may be substituted, an alkoxycarbonyl, group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted and a heterocyclic group which may be substituted;

$R^3$ is a hydrogen atom, an alkoxy group which may be substituted, an aryloxy group which may be substituted, an aralkyloxy group which may be substituted, a hydroxy group and a hydrocarbon group which may be substituted;

$R^4$ is an alkoxy group which may be substituted, an aryloxy group which may be substituted, an aralkyloxy group which may be substituted, a hydroxy group, —NR$^a$R$^b$ [wherein R$^a$ and R$^b$ are each independently a hydrogen atom, a hydrocarbon group which may be substituted and an acyl group which may be substituted, —SO$_2$A$^1$ (wherein A$^1$ is a hydrocarbon group which may be substituted or a substituted amino group), or —COOR$^c$ (R$^c$ is a hydrocarbon group which may be substituted)] or a heterocyclic group which may be substituted, and $R^1$ and $R^2$, or $R^2$ and $R^3$ each may combine to form a ring; with the proviso that when $R^1$=$R^2$, then $R^3$ is a hydrocarbon group which may be substituted;

Q is a group formed by removing a hydrogen atom from an amine; and

* indicates an asymmetric carbon atom;

or a salt thereof, which comprises reacting an α,β-unsaturated carboxylic acid derivative of the formula (1):

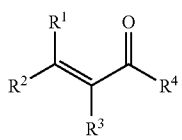

(1)

wherein $R^1$ to $R^4$ are each the same as mentioned above, with an amine or a salt thereof, in the presence of a chiral catalyst and in the presence of an acid.

2. The process according to claim 1, wherein said amine or acid salt thereof is a compound of the formula (3):

(3)

wherein $R^5$ and $R^{55}$ are each independently a hydrogen atom, a hydrocarbon group which may be substituted, an alkoxy group which may be substituted, an aryloxy group which may be substituted or an aralkyloxy group which may be substituted; X is an acid; and a is 0 or 1.

3. The process according to claim 1, wherein said optically active β-amino acid or salt thereof is a compound of the formula (4):

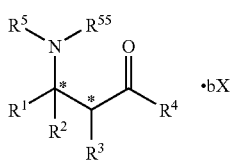

(4)

wherein $R^1$ and $R^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted or a heterocyclic group which may be substituted;

$R^3$ is a hydrogen atom, an alkoxy group which may be substituted, an aryloxy group which may be substituted, an aralkyloxy group which may be substituted, a hydroxy group or a hydrocarbon group which may be substituted;

$R^4$ is an alkoxy group which may be substituted, an aryloxy group which may be substituted, an aralkyloxy group which may be substituted, a hydroxy group, —NR$^a$R$^b$ [wherein R$^a$ and R$^b$ are each independently a hydrogen atom, a hydrocarbon group which may be substituted, an acyl group which may be substituted, —SO$_2$A$^1$ (wherein A$^1$ is a hydrocarbon group which may be substituted or a substituted amino group), or —COOR$^c$ (R$^c$ is a hydrocarbon group which may be substituted)] or a heterocyclic group which may be substituted;

R$^5$ and R$^{55}$ are each independently a hydrogen atom, a hydrocarbon group which may be substituted, an alkoxy group which may be substituted, an aryloxy group which may be substituted or an aralkyloxy group which may be substituted;

b is 0 or 1;

X is an acid;

* indicates an asymmetric carbon; or

R$^1$ and R$^2$, or R$^2$ and R$^3$ may combine to form a ring, with the proviso that when R$^1$=R$^2$, then R$^3$ is a hydrocarbon group which may be substituted.

4. The process according to claim 1, wherein the chiral catalyst is a chiral transition-metal complex of the formula (5):

  (5)

wherein L is a chiral ligand; Z$^-$ is a counter anion; A is an anionic ligand selected from the group consisting of a hydroxy group, an amide group, an alkoxy group and a halogen atom; M is a transition metal; y is 0 or 2; q is 2; p is 2 or 4, or of the formula (6):

  (6)

wherein L is a chiral ligand; Z$^-$ is a counter anion; B is a water molecule or a neutral ligand; M is a transition metal; r is 1 or 2; s is 0, 1, 2, 4 or 6; c is 0, 1 or 2.

5. The process according to claim 1, wherein the α,β-unsaturated carboxylic acid derivative of the formula (1):

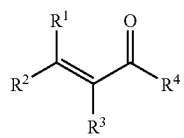  (1)

wherein R$^1$ and R$^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted, or a heterocyclic group which may be substituted;

R$^3$ is a hydrogen atom, an alkoxy group which may be substituted, an aryloxy group which may be substituted, an aralkyloxy group which may be substituted, a hydroxy group, or a hydrocarbon group which may be substituted;

R$^4$ is an alkoxy group which may be substituted, an aryloxy group which may be substituted, an aralkyloxy group which may be substituted, a hydroxy group, —NR$^a$R$^b$ [wherein R$^a$ and R$^b$ are each independently a hydrogen atom, a hydrocarbon group which may be substituted, an acyl group which may be substituted, —SO$^2$A$^1$ (wherein A$^1$ is a hydrocarbon group which may be substituted or a substituted amino group), or —COOR$^c$ (R$^c$ is a hydrocarbon group which may be substituted)], or a heterocyclic group which may be substituted; or R$^1$ and R$^2$, or R$^2$ and R$^3$ may combine to form a ring, with the proviso that when R$^1$=R$^2$, then R$^3$ is a hydrocarbon group which may be substituted, is reacted with a primary amine of the formula (3b):

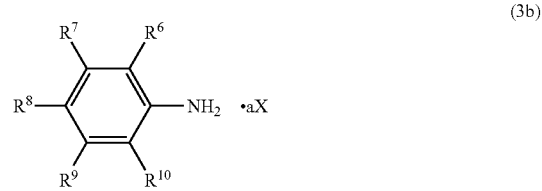  (3b)

wherein a is 0 or 1; R$^6$ to R$^{10}$ are each independently a hydrogen atom, a hydrocarbon group which may be substituted, a halogen atom, a heterocyclic group which may be substituted, an alkoxy group which may be substituted, an aralkyloxy group which may be substituted, an aryloxy group which may be substituted, an acyl group which may be substituted, an acyloxy group, an alkoxycarbonyl group which may be substituted, an aryloxycarbonyl group which may be substituted, an aralkyloxycarbonyl group which may be substituted, an alkylenedioxy group, a hydroxy group, a nitro group or an amino group which may be substituted; or R$^6$ and R$^7$, R$^7$ and R$^8$, R$^8$ and R$^9$, or R$^9$ and R$^{10}$ each may combine to form a fused ring, with the proviso that at least one of R$^6$ to R$^{10}$ is a halogenated hydrocarbon group; and X is an acid, or a salt thereof in the presence of an acid and in the presence of a chiral catalyst, to produce an optically active β-amino acid derivative of the formula (4a):

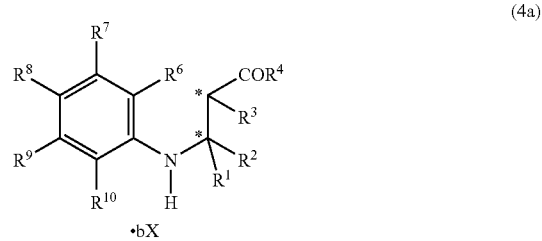  (4a)

wherein b is 0 or 1; * indicates an asymmetric carbon; and R$^1$ to R$^{10}$, a and X are each the same as defined above.

6. The process according to claim 4, wherein the chiral transition-metal complex of the formula (5) or (6) is selected from the group consisting of Pd((R)-binap)(H$_2$O)$_2$(OTf)$_2$, Pd((S)-dm-binap)(H$_2$O)$_2$(OTf)$_2$, Pd((R)-segphos)(H$_2$O)$_2$(OTf)$_2$ and Pd((R)-binap)(μ-OH)$_2$(OTf)$_2$.

7. A process for producing an optically active β-amino acid derivative of the formula (2):

  (2)

wherein R$^1$ and R$^2$ are each independently a hydrogen atom, a hydrocarbon group which may be substituted, an acyl group which may be substituted, an alkoxycarbonyl group which may be substituted, an aryloxycarbonyl group which may be substituted, an aralkyloxycarbonyl group which may be substituted, an alkoxy group which may be substituted, an aryloxy group which may be substituted, an aralkyloxy group which may be substituted and a heterocyclic group which may be substituted;

$R^3$ is a hydrogen atom, an alkoxy group which may be substituted, an acyloxy group which may be substituted, an aralkyloxy group which may be substituted, a hydroxy group and a hydrocarbon group which may be substituted;

$R^4$ is an alkoxy group which may be substituted, an aryloxy group which may be substituted, an aralkyloxy group which may be substituted, a hydroxy group, —$NR^aR^b$ [wherein $R^a$ and $R^b$ are each independently a hydrogen atom, a hydrocarbon group which may be substituted and an acyl group which may be substituted, —$SO_2A^1$ (wherein $A^1$ is a hydrocarbon group which may be substituted or a substituted amino group), or —$COOR^c$ ($R^c$ is a hydrocarbon group which may be substituted)] or a heterocyclic group which may be substituted, and $R^1$ and $R^2$, or $R^2$ and $R^3$ each may combine to form a ring; with the proviso that when $R^1=R^2$, then $R^3$ is a hydrocarbon group which may be substituted;

Q is a group formed by removing a hydrogen atom from an amine; and

* indicates an asymmetric carbon atom;
or a salt thereof, which comprises reacting an α,β-unsaturated carboxylic acid derivative of the formula (1):

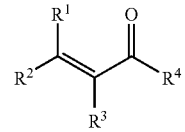

(1)

wherein $R^1$ to $R^4$ are each the same as mentioned above, with an amine or a salt thereof, in the presence of a chiral catalyst, wherein the chiral catalyst is a chiral transition-metal complex of the formula (5):

$$[M_2L_pA_q]^{p+}(Z^-)_y \qquad (5)$$

wherein L is a chiral ligand; $Z^-$ is a counter anion; A is an anionic ligand selected from the group consisting of a hydroxy group, an amide group, an alkoxy group and a halogen atom; M is a transition metal; y is 0 or 2; q is 2; p is 2 or 4, or of the formula (6):

$$ML_rB_s(Z^-)_c \qquad (6)$$

wherein L is a chiral ligand; $Z^-$ is a counter anion; B is a water molecule or a neutral ligand; M is a transition metal; r is 1 or 2; s is 0, 1, 2, 4 or 6; c is 0, 1 or 2, and in the presence of an acid.

* * * * *